United States Patent
Tokeshi et al.

(10) Patent No.: US 12,269,001 B2
(45) Date of Patent: Apr. 8, 2025

(54) FLOW CHANNEL STRUCTURE AND LIPID PARTICLE OR MICELLE FORMATION METHOD USING SAME

(71) Applicant: National University Corporation Hokkaido University, Sapporo (JP)

(72) Inventors: Manabu Tokeshi, Sapporo (JP); Masatoshi Maeki, Sapporo (JP); Yusuke Sato, Sapporo (JP); Hideyoshi Harashima, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 1190 days.

(21) Appl. No.: 16/605,138

(22) PCT Filed: Apr. 13, 2018

(86) PCT No.: PCT/JP2018/015550
§ 371 (c)(1),
(2) Date: Oct. 14, 2019

(87) PCT Pub. No.: WO2018/190423
PCT Pub. Date: Oct. 18, 2018

(65) Prior Publication Data
US 2021/0129103 A1 May 6, 2021

(30) Foreign Application Priority Data

Apr. 13, 2017 (JP) .............................. JP2017-080118

(51) Int. Cl.
*B01J 13/04* (2006.01)
*A61K 9/127* (2006.01)
(Continued)

(52) U.S. Cl.
CPC ............. *B01J 13/04* (2013.01); *A61K 9/1277* (2013.01); *B01J 19/0093* (2013.01);
(Continued)

(58) Field of Classification Search
None
See application file for complete search history.

(56) References Cited

U.S. PATENT DOCUMENTS

2003/0031090 A1 2/2003 Ho et al.
2014/0328759 A1* 11/2014 Cullis ..................... A61P 25/24
424/490
(Continued)

FOREIGN PATENT DOCUMENTS

CN 101618308 A 1/2010
JP 2006-167600 A 6/2006
(Continued)

OTHER PUBLICATIONS

Office Action issued in Chinese Patent Application No. 201880024696.8 dated Aug. 4, 2021.
(Continued)

*Primary Examiner* — Jeffrey D Washville
(74) *Attorney, Agent, or Firm* — Marshall, Gerstein & Borun LLP

(57) ABSTRACT

Provided are: a flow channel structure with which lipid particles or micelles, which are useful as nano-sized carriers, for example, in drug delivery systems, are produced with good control of particle size; and a method for forming lipid particles or micelles using the same. Said flow channel structure has a two-dimensional structure such as one in which multiple structural elements (baffles) of a specified width are alternately disposed from the two side faces in a micro-sized flow channel through which feedstock solutions are flowed.

23 Claims, 15 Drawing Sheets

(51) Int. Cl.
    *A61K 9/1277*      (2025.01)
    *B01J 19/00*      (2006.01)
    *B82Y 5/00*      (2011.01)

(52) U.S. Cl.
    CPC ............ *B01J 2219/0086* (2013.01); *B01J 2219/00894* (2013.01); *B01J 2219/00959* (2013.01); *B82Y 5/00* (2013.01)

(56) References Cited

U.S. PATENT DOCUMENTS

| | | | |
|---|---|---|---|
| 2015/0115488 | A1 | 4/2015 | Hood et al. |
| 2021/0023514 | A1* | 1/2021 | Ramsay ............ B01F 25/43231 |

FOREIGN PATENT DOCUMENTS

| | | |
|---|---|---|
| JP | 2013510096 A | 3/2013 |
| JP | 2015-502337 A | 1/2015 |
| JP | 6942376 B2 | 9/2021 |
| TW | 201709926 A | 3/2017 |
| WO | WO-2011/140627 A1 | 11/2011 |
| WO | WO-2013-059922 A1 | 5/2013 |
| WO | WO-2016/138175 A1 | 9/2016 |
| WO | WO-2016/172511 A1 | 10/2016 |

OTHER PUBLICATIONS

Office Action issued in Indian Patent Application No. 201927045837 dated Sep. 16, 2021.
Office Action issued in Taiwanese Patent Application No. 107112803 dated Jul. 6, 2020.
Office Action issued in Canadian Patent Application No. 3,059,714 dated Nov. 30, 2021.
Supplementary European Search Report issued in European Patent Application No. 18784715 dated Nov. 27, 2020.
International Preliminary Report on Patentability issued in PCT Patent Application No. PCT/JP2018/015550 dated Oct. 17, 2019.
International Search Report issued in PCT Patent Application No. PCT/JP2018/015550 dated Jun. 26, 2018.
Chang et al., "Computational analysis of electrokinetically driven flow mixing in microchannels with patterned blocks," *Journal of Micromechanics and Microengineering*, vol. 14 (2004).
"Iyaku Genyaku no Seizou, Dai 19 Kai, Ki ni naru Seizo Sochi 1: Microreactor (1)" Retrieved from the Internet: <URL:http://www.gmp-platform.com/topics_detaill/id=2477>.
Maeki et al., "A strategy for synthesis of lipid nanoparticles using microfluidic devices with a mixture structure," *RSC Advances*, 5, 46181 (2015).
Sato et al., "Elucidation of the physicochemical properties and potency of siRNA-loaded small-sized lipid nanoparticles for siRNA delivery," *Journal of Controlled Release*, 229, pp. 48-57 (2016).
Zhigaltsev et al., "Bottom-up Design and Synthesis of Limit Size Lipid Nanoparticle Systems with Aqueous and Triglyceride cores Using Millisecond Microfluidic Mixing," *Langmuir*, 28, pp. 3633-3640 (2012).
Chen et al., "Rapid Discovery of Potent siRNA-Containing Lipid Nanoparticles Enabled by Controlled Microfluidic Formulation," *Journal of the American Chemical Society*, 134, pp. 6948-6951 (2012).
Stroock et al., "Chaotic Mixer for Microchannels," *Science*, vol. 295, pp. 647-651 (Jan. 2002).
Office Action issued in European Patent Application No. 18784715.7 dated Feb. 21, 2022.
Office Action issued in Chinese Patent Application No. 201880024696.8 dated Feb. 25, 2022.
Naher, S. et al., "Effect of micro-channel geometry on fluid flow and mixing," *Simulation Modelling Practice and Theory*, vol. 19, p. 1088-1095 (2010).
Wang, D. et al., "Modelling of electrokinetically driven mixing flow in microchannels with patterned blocks," *Computers and Mathematics with Applications*, vol. 55, pp. 1601-1610 (2008).
Office Action, Chinese Application No. 201880024696.8, dated Jul. 13, 2022.
Office Action issued in Japanese Patent Application No. 2021-142077 dated Sep. 27, 2022.
Office Action issued in Japanese Patent Application No. 2021-142077, dated Dec. 13, 2022.

* cited by examiner

BASIC FLOW CHANNEL STRUCTURE

OBSERVATION OF LIVER WITH CONFOCAL LASER SCANNING MICROSCOPE 30 MINUTES AFTER INTRAVENOUS ADMINISTRATION TO MICE

3% PEG HAVING SMALL PARTICLE DIAMETER DEMONSTRATED LITTLE NON-SPECIFIC ACCUMULATION IN BLOOD VESSELS AND SELECTIVELY REACHED LIVER PARENCHYMAL CELLS (DEEP PART OF TISSUE)

(a)

(b)

FLOW CHANNEL STRUCTURE AND LIPID PARTICLE OR MICELLE FORMATION METHOD USING SAME

TECHNICAL FIELD

The present invention relates to a flow channel structure and a lipid particle or micelle formation method that uses that flow channel structure. More particularly, the present invention relates to a flow channel structure for producing lipid particles or micelles such as amphipathic polymers with a high degree of particle diameter controllability for use as nano-sized carriers in drug delivery systems, for example, and to a lipid particle or micelle formation method using that flow channel structure.

BACKGROUND ART

Practical application of lipid nanoparticles is proceeding to the greatest degree for use as nanocarriers for drug delivery systems (DDS), and these nanocarriers are already being used clinically. Recently, it has been determined that the delivery efficiency of a drug into cancer tissue varies according to the particle diameter of the nanocarrier. In addition, since the delivery efficiency to an organ differs according to the particle diameter of the carrier, control of particle diameter for such lipid nanoparticles is becoming increasingly important. However, in the case of preparing lipid nanoparticles by conventionally known methods such as extrusion or ultrasonic treatment, it is difficult to precisely prepare lipid nanoparticles having a particle diameter of about 10 nm to 100 nm, which are considered to demonstrate high delivery efficiency to cancer tissue and other tissue, for example, of an arbitrary size within this range of particle diameter with little variation.

Meanwhile, microdevices have been reported to be able to prepare lipid nanoparticles in which particle diameter is precisely controlled (NPL 1 to 4). However, since microdevices that have been reported thus far use a three-dimensional mixer structure, it is difficult to fabricate and process microdevices per se. In addition, since the range of particle diameter at which lipid nanoparticles can be prepared is narrow, there is a desire for the development of a lipid nanoparticle formation system that demonstrates higher particle diameter controllability.

Thus, an object of the present invention is to provide a flow channel structure that solves the technical problem described above and a lipid particle formation method that uses that flow channel structure. In addition, an object of the present invention is to provide a flow channel structure for producing lipid particles or micelles such as amphipathic polymers with a high degree of particle diameter controllability for use as nano-sized carriers in drug delivery systems, for example, and to a lipid particle or micelle formation method using that flow channel structure.

CITATION LIST

Non Patent Literature

[NPL 1] "A Strategy for Synthesis of Lipid Nanoparticles Using Microfluidic Devices with a Mixer Structure", M. Maeki, T. Saito, Y. Sato, T. Yasui, N. Kaji, A. Ishida, H. Tani, Y. Baba, H. Harashima and M. Tokeshi, RSC Advances, 5, 46181, (2015).

[NPL 2] "Elucidation of the Physicochemical Properties and Potency of siRNA-Loaded Small-Sized Lipid Nanoparticles for siRNA Delivery", Y. Sato, Y. Note, M. Maeki, N. Kaji, Y. Baba, M. Tokeshi and H. Harashima, Journal of Controlled Release, 229, 48, (2016).

[NPL 3] "Bottom-Up Design and Synthesis of Limit Size Lipid Nanoparticle Systems with Aqueous and Triglyceride Cores Using Millisecond Microfluidic Mixing", I. V. Zhigaltsev, N. Belliveau, I. Hafez, A. K. K. Leung, C. Hansen and P. R. Cullis, Langmuir, 38, 3633, (2012).

[NPL 4] "Rapid Discovery of Protein siRNA-Containing Lipid Nanoparticles Enabled by Controlled Microfluidic Formation", D. Chen, K. T. Love, Y. Chen, A. A. Eltoukhy, C. Kastrup, G. Sahay, A. Jeon, Y. Dong, K. A. Whitehead and D. G. Anderson, Journal of the American Chemical Society, 134, 6948, (2012).

SUMMARY OF THE DISCLOSURE

As has been described above, although conventional microdevices form nano-sized lipid particles by mixing a feedstock solution by generating chaotic advection using a three-dimensional mixer structure, as a result thereof, control of the fluid behavior of the feedstock solution is difficult and the range of particle diameter over which lipid particles can be prepared is narrow. As a result of conducting extensive studies and research on the basis of this technical background, the inventors of the present invention conceived a nano-sized lipid particle formation system using a flow channel structure having a simple, two-dimensional structure such that baffles of a fixed width are alternately disposed from both side surfaces in a micro-sized flow channel through which a feedstock solution flows in order to precisely prepare lipid particles of a target size. Baffles of a constant width are installed relative to the flow channel width of the micro-sized flow channel. Differing from a conventional three-dimensional mixer structure, mixing and dilution with this two-dimensional microchannel are dependent on molecular diffusion. Thus, it was found that the dilution rate of the feedstock solution can be controlled by adjusting the width, length and arrangement of the baffles, and that a nano-sized lipid particle formation system can be formed having a higher degree of particle diameter controllability than the prior art. Moreover, nano-sized micelles were also confirmed to be able to be similarly formed with a high degree of particle diameter controllability using, for example, a polymer such as an amphipathic block copolymer, without being limited to lipid particles, thereby leading to completion of the present invention.

Namely, the present invention that solves the aforementioned problem is a flow channel structure for forming nano-sized lipid particles or micelles, wherein in the flow channel structure, a mutually independent first inlet channel that introduces a first fluid and a second inlet channel that introduces a second fluid join together and have respectively fixed lengths on the upstream side thereof and a single dilution flow channel is formed towards the downstream side thereof, the dilution flow channel has a bent flow channel site that is bent two-dimensionally in at least a portion thereof, and the bent flow channel site is such that, in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$, at least two or more structural elements, which define flow channel width of the dilution flow channel by alternately protruding from both side surfaces of the dilution flow channel in opposition to the Y direction towards the center of the flow channel at a fixed height $h_1, h_2, \ldots$ of $1/2y_0$ or more and less than $1y_0$ in an approximate Y direction (approximate+Y direction or approximate −Y direction) and at a fixed width $x_1, x_2, \ldots$ in the X direction, are provided at fixed intervals $d_1, d_2, \ldots$ In the flow channel structure according to the present invention, an aspect is included wherein the flow channel width $y_0$ is 20 μm to 1000 μm, the width of each structural element $x_1, x_2, \ldots$ is 20 μm to 1000 μm, and the interval $d_1, d_2, \ldots$ between each structural element is 20 μm to 1000 μm.

In addition, in the flow channel structure according to the present invention, an aspect is included wherein 10 to 100 structural elements are provided.

Moreover, in the flow channel structure according to the present invention, an aspect is included wherein the distance from the confluence of the first inlet channel and the second inlet channel to the upstream end of the first structural element is defined corresponding to the set speed of the dilution fluid so that dilution fluid at a set speed flowing there between passes through in 0.1 seconds or less.

Moreover, in the flow channel structure according to the present invention, an aspect is included wherein a plurality of flow channels is respectively provided as the first inlet channel and/or the second inlet channel.

Moreover, in the flow channel structure according to the present invention, an aspect is included wherein the approximate Y direction is a direction that intersects the flow channel direction (X direction) at an angle of 40° to 140°.

Namely, the present invention that solves the aforementioned problem is a flow channel structure for forming nano-sized lipid particles or micelles, wherein in the flow channel structure, a mutually independent first inlet channel that introduces a first fluid and a second inlet channel that introduces a second fluid join together and have respectively fixed lengths on the upstream side thereof and a single dilution flow channel is formed towards the downstream side thereof, the dilution flow channel has a bent flow channel site that is bent two-dimensionally in at least a portion thereof, and the bent flow channel site is such that, in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$, at least two or more structural elements, which define flow channel width of the dilution flow channel by alternately protruding from both side surfaces of the dilution flow channel in opposition to the Y direction towards the center of the flow channel at a fixed height $h_1, h_2, \ldots$ of $1/2y_0$ or more and less than $1y_0$ in an approximate Y direction (approximate +Y direction or approximate −Y direction) and at a fixed width $x_1, x_2, \ldots$ in the X direction, are provided at fixed intervals $d_1, d_2, \ldots$ The present invention that solves the aforementioned problem is a lipid particle or micelle formation method for forming nano-sized lipid particles or micelles by diluting a lipid solution or amphipathic substance solution with a dilution medium in a flow channel structure, wherein the flow channel structure forms a single dilution flow channel towards the downstream side thereof by joining together a mutually independent first inlet channel and second inlet channel having respectively fixed lengths on the upstream side, the dilution flow channel has a flow channel site that is bent two-dimensionally in at least a portion thereof, the bent flow channel site is such that, in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$, at least two or more structural elements, which define flow channel width of the dilution flow channel by alternately protruding from both side surfaces of the dilution flow channel in opposition to the Y direction towards the center of the flow channel at a fixed height $h_1, h_2, \ldots$ of $1/2y_0$ or more and less than $1y_0$ in an approximate Y direction (approximate +Y direction or approximate −Y direction) and at a fixed width $x_1, x_2, \ldots$ in the X direction, are provided at fixed intervals $d_1, d_2, \ldots$, and utilizes this characteristic to introduce the lipid solution or amphipathic substance solution from one of the first inlet channel and second inlet channel of the flow channel structure and introduces the dilution solvent from the other inlet channel at a total flow rate of 1 μl/min to 100 ml/min.

As a result of forming lipid particles or micelles using the flow channel structure according to the present invention, lipid particles or micelles can be precisely prepared at an arbitrary size within a particle diameter range of, for example, about 10 nm to 100 nm with little variation, thereby making it possible to provide lipid particles or micelles useful as carriers for efficient drug delivery systems (DDS).

DETAILED DESCRIPTION OF EMBODIMENTS

The following provides an explanation of the present invention based on preferred embodiments thereof. Furthermore, although the following explanation of the present invention focuses primarily on the case of forming lipid particles (liposomes), unless specifically indicated otherwise, the following contents described in detail should be understood to be similarly applicable to the case of forming micelles of various types of amphipathic molecules having an amphipathic molecule having a solvent-soluble portion and an insoluble portion within the same molecule in the manner of, for example, an amphipathic block copolymer, as a constituent unit thereof and in which the Van Der Waals force of the insoluble portion serves as the driving force.

Flow Channel Structure

An explanation is first provided of the flow channel structure of the present invention.

Figure 1:
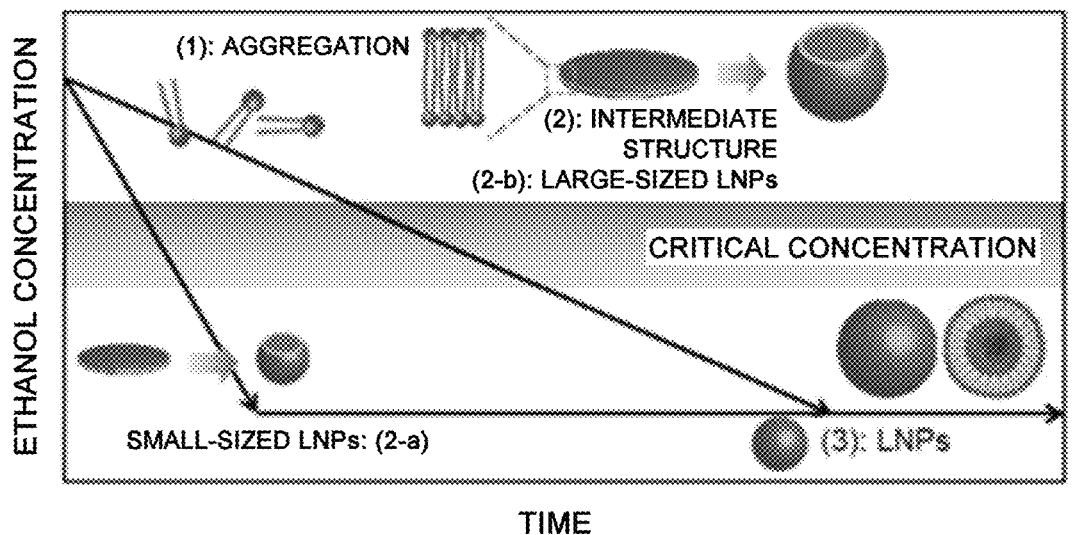
FIG. 1 is an overview explaining the formation principle of lipid particles.

Generally speaking, the flow channel structure of the present invention is a flow channel structure having a two-dimensional structure such that structural elements (baffles) of a fixed width and roughly rectangular shape are mutually differently arranged from both side surfaces in the flow channel of a microdevice through which a feedstock solution flows. Differing from conventional three-dimensional mixer structures, dilution in this type of two-dimensional micro flow channel is dependent on molecular diffusion. Namely, as shown in FIG. 1, the size of lipid particles formed becomes smaller the faster the dilution rate of the lipid solution serving as feedstock. Thus, the dilution rate of the feedstock solution can be controlled by adjusting the width, length and arrangement of the structural elements (baffles), thereby making it possible to form nano-sized lipid particles having a higher degree of particle diameter controllability than in the prior art.

Figure 2:
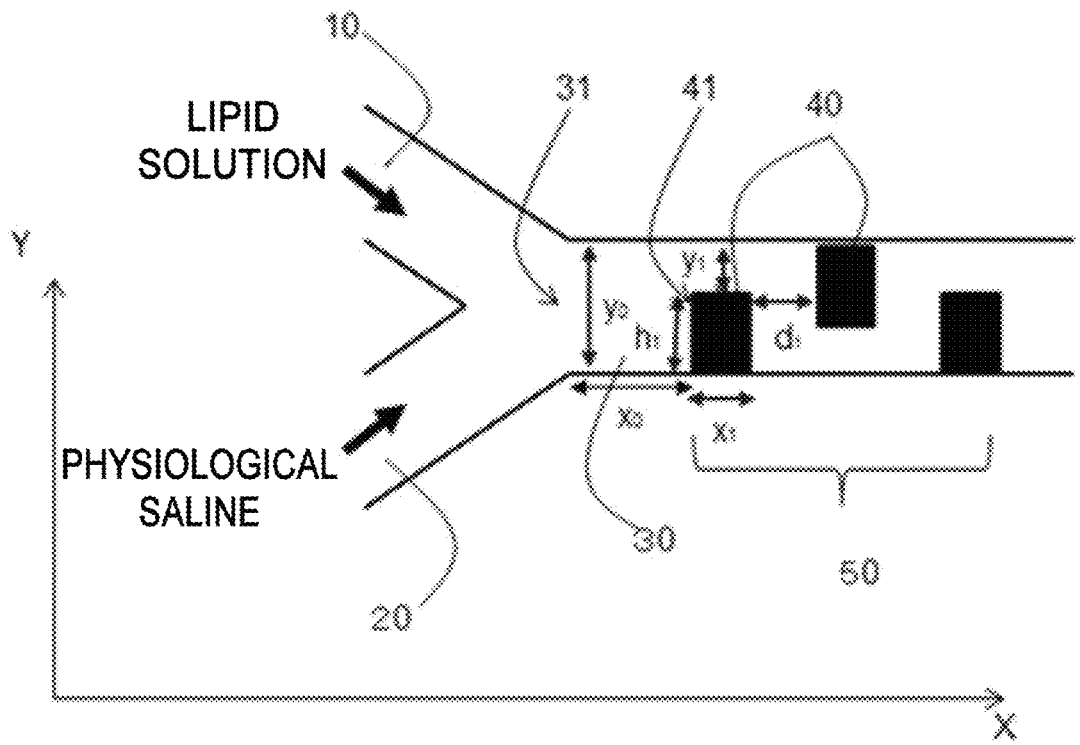
FIG. 2 is a drawing schematically showing the structure in one embodiment of the flow channel structure according to the present invention.

Namely, the flow channel structure according to the present invention is a flow channel structure for forming nano-sized lipid particles or micelles of an amphipathic substance such as an amphipathic polymer (and in the following description, "lipid particles or micelles of an amphipathic substance" may be simply referred to as "lipid particles" for the sake of simplification), and as is schematically shown in FIG. 2, for example, a mutually independent first inlet channel 10 that introduces a first fluid and a second inlet channel 20 that introduces a second fluid join together and have respectively fixed lengths on the upstream side thereof (left side in the drawing) to form a single dilution flow channel 30 towards the downstream side, the dilution flow channel 30 has a flow channel site that 50 is bent two-dimensionally in at least a portion thereof, and the bent flow channel site 50 is such that, in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$, at least two or more structural elements 40, which define flow channel width of the dilution flow channel by alternately protruding from both side surfaces of the dilution flow channel in opposition to the Y direction towards the center of the flow channel at a fixed height $h_1$, $h_2$, ... of $1/2y_0$ or more and less than $1y_0$ in an approximate Y direction (approximate +Y direction or approximate −Y direction) and at a fixed width $x_1, x_2, \ldots$ in the X direction, are provided at fixed intervals $d_1, d_2, \ldots$. Namely, at the site where the structural elements 40 are present, a flow channel width $y_1, y_2, \ldots$ of the dilution flow channel is restricted to $1/2y_0$ or less, and particularly, $1/2y_0$ or less to $1/40y_0$ or more between a fixed width $x_1, x_2, \ldots$ in the X direction.

Figure 3:
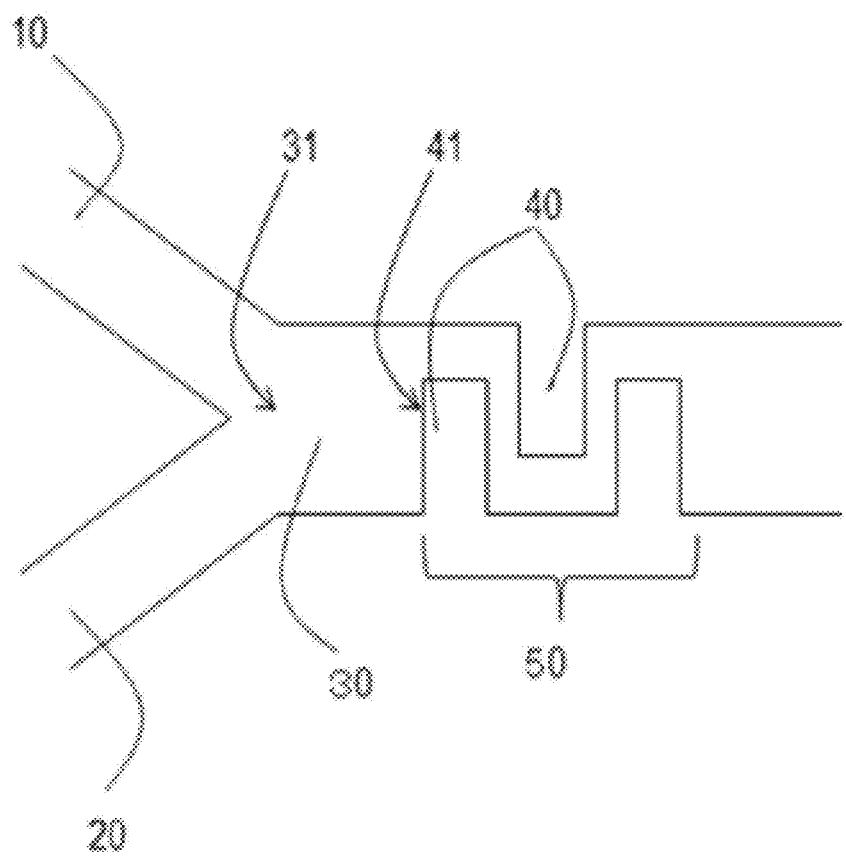
FIG. 3 is a drawing schematically showing an example of the configuration of a different embodiment of the flow channel structure according to the present invention.

Furthermore, although the flow channel structure according to the present invention conceptually has a form such that roughly rectangular baffles are mutually differently arranged from both side surfaces in the flow channel of a microdevice as exemplified in FIG. 2 and explained above, in actuality, the flow channel structure is not limited to that composed by arranging separate baffles in a flow channel in this manner. Namely, there are no particular limitations on the configuration of the structural elements 40 provided a flow channel of a similar form is formed so as to correspond to a flow channel formed by arranging such baffles, and as shown in FIG. 3, for example, may be that which composes the form of a flow channel having a two-dimensional structure in which the walls of a flow channel structure bend in a prescribed shape (while maintaining a nearly fixed wall thickness) while being integrally formed to bend and expand so as to be defined as previously described so as to compose the structural elements 40 in the manner previously described, and such an aspect is naturally included in the flow channel structure according to the present invention. The configuration like that shown in FIG. 3 can be formed relatively easily by injection molding, cast molding or molding using a three-dimensional printer using, for example, a thermoplastic resin, thermosetting resin, ultraviolet curable resin or metal or vitreous material.

Figure 8:
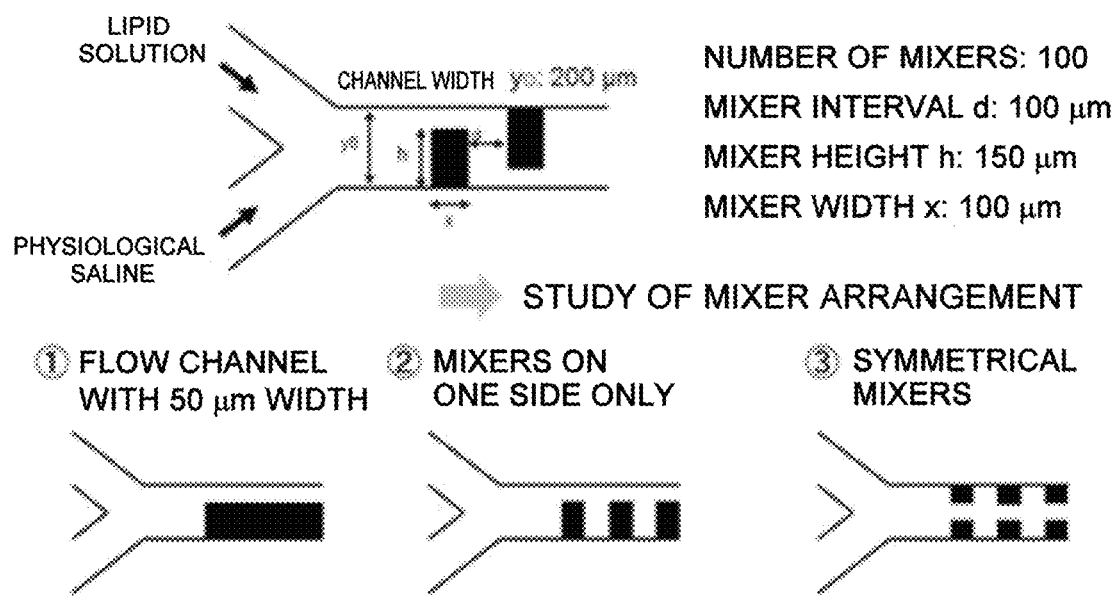
FIG. 8 is a drawing schematically showing an arrangement of structural elements in a flow channel structure used in an example.

In the flow channel structure according to the present invention, the formation of a bent flow channel site 50, which is bent into a shape in which the structural elements 40 as described above are mutually differently arranged from walls on both sides of a dilution flow channel, is important in terms of enhancing dilution efficiency with a dilution solvent of a lipid solution or amphipathic substance solution (and in the following description, "a lipid solution or amphipathic substance solution" may be simply referred to as a "lipid solution" for the sake of simplification) and obtaining nano-sized lipid particles or micelles that have been controlled to a desired particle diameter. For example, although possible examples of shapes resembling the arrangement of the structural elements 40 according to the present invention include, as shown in FIG. 8, (1) a shape such that a single structural element 40 of the same height but greater width is provided on one sidewall, (2) a shape such that a plurality of structural elements 40 of the same height are provided only on one sidewall, and (3) a shape such that a plurality of structural elements 40 are respectively symmetrically arranged on both sidewalls and the height of each structural element is roughly half, in these forms, when compared with the bent flow channel site 50 in the flow channel structure according to the present invention, adequate molecular diffusion is unable to proceed in a short period of time and nano-sized lipid particles controlled to a desired particle diameter are unable to be obtained perhaps due to the flow channel structure being overly simple.

Although the flow channel width $y_0$ of the dilution flow channel 30 after the first inlet channel 10 and the second inlet channel 20 have joined together is influenced to a certain degree by the size of the particle diameter of the nano-sized lipid particles to be formed, this value is typically about 20 μm to 1000 μm and more preferably about 100 μm to 200 μm. In terms of obtaining desired nano-sized lipid particles, and more specifically, lipid particles having a particle diameter of a size that is within the particle diameter range of, for example, about 10 nm to 100 nm, diluting the lipid solution with a dilution medium at the flow channel width $y_0$ within the range described above is, to a certain degree, a required condition.

Next, although the number of the structural elements 40 arranged in plurality in the flow channel structure according to the present invention in order to form the bent flow channel site 50 that provides a site for substantial molecular diffusion is influenced by other conditions such as the size of the lipid particles to be obtained, the height $h_1, h_2, \ldots$ (length in Y direction) and width $x_1, x_2, \ldots$ (length in X direction) of each of the structural elements 40, and distance $d_1, d_2, \ldots$ between each adjacent structural element 40, at least 2 or more, preferably 10 or more and more preferably about 10 to 100 are desirable since lipid particles of an intended size can be formed. Furthermore, there are no particular limitations on the upper limit of the number of structural elements 40 from the viewpoint of forming lipid particles of a prescribed particle size, and in principle, for example, 1000 or more or even 10000 or more still make it possible to form similar lipid particles of a prescribed particle size. However, if that number is extremely large, the flow channel structure is not very practical from the viewpoints of causing an increase in fluid resistance during the flow of feedstock and an increase in fabrication costs of the flow channel structure.

In addition, the height $h_1, h_2, \ldots$ (length in the Y direction) of each structural element 40 is $1/2y_0$ or more and less than $1y_0$, preferably $1/2y_0$ or more and $39/40y_0$ or less, and even more preferably $1/2y_0$ or more and $3/4y_0$ or less relative to the flow channel width $y_0$ of the dilution flow channel 30 on the upstream side therefrom, and due to the presence of each structural element 40, flow channel width $y_1, y_2, \ldots$ is decreased from the flow channel width $y_0$ of the dilution flow channel 30 on the upstream side therefrom to a width of less than $1/2y_0$ and greater than 0. Furthermore, the respective height $h_1, h_2, \ldots$ of the plurality of structural elements 40 provided in the bent flow channel site 50 is not necessarily required to be the same, but rather may each be different provided the above-mentioned prescribed conditions are satisfied. The flow channel widths $y_1, y_2, \ldots$ formed as a result thereof may also each be different. For example, an aspect may be employed in which the each width $h_1, h_2, \ldots$ of each structural element 40 may gradually become longer and flow channel width $y_1, y_2, \ldots$ may become narrower moving in the downstream direction. The efficiency of molecular diffusion improves as a result of the height $h_1, h_2, \ldots$ (length in Y direction) of each structural element 40 being a prescribed height and the flow channel widths $y_1, y_2, \ldots$ of the sites where these structural elements 40 are present being held to a width of less than $1/2y_0$.

Although influenced by other conditions such as the size of the lipid particles to be obtained, the number of structural elements 40, the width $x_1, x_2, \ldots$ (length in the X direction) of each mixer structural element 40 or the distance $d_1, d_2, \ldots$ between each adjacent structural element 40, and there are no particular limitations thereon, more specifically, in the case, for example, the flow channel width $y_0$ of the upstream dilution flow channel is 200 μm, then the respective height $h_1, h_2, \ldots$ of the structural elements 40 is preferably 100 μm to less than 200 μm. Thus, the flow channel width $y_1, y_2, \ldots$ at the location where each structural element 40 is present is roughly less than 100 μm, which is less than $1/2y_0$ and greater than 0.

In addition, although influenced by other conditions such as the size of the lipid particles to be obtained, the number of the structural elements 40, the height $h_1, h_2, \ldots$ (length in the Y direction) of each structural element 40 or the interval $d_1, d_2, \ldots$ between each adjacent structural element 40, the width $x_1, x_2, \ldots$ (length in the X direction) of each structural element 40 is preferably a length of about $1/10 y_0$ or more and $5 y_0$ or less relative to the flow channel width $y_0$ of the upstream dilution flow channel. More specifically, in the case, for example, the flow channel width $y_0$ of the upstream dilution flow channel is 20 μm to 1000 μm, and typically 200 μm, the respective width $x_1, x_2, \ldots$ of the structural elements 40 is preferably about 20 μm to 1000 μm. The respective width $x_1, x_2, \ldots$ of each structural element 40 is not necessarily required to be the same and may each be different provided the above-mentioned prescribed conditions are satisfied. For example, an aspect may be employed in which the width $x_1, x_2,$ gradually becomes longer moving in the downstream direction.

In addition, although influenced by other conditions such as the size of the lipid particles to be obtained, the number of the structural elements 40, the height $h_1, h_2, \ldots$ (length in the Y direction) of each structural element 40 or the width $x_1, x_2, \ldots$ (length in the X direction) of each adjacent structural element 40, the interval $d_1, d_2, \ldots$ between each adjacent structural element 40 is preferably a length of about $1/10 y_0$ or more and $5 y_0$ or less relative to the flow channel width $y_0$ of the upstream dilution flow channel. More specifically, in the case, for example, the flow channel width $y_0$ of the upstream dilution flow channel is 20 μm to 1000 μm, and typically 200 μm, the interval $d_1, d_2, \ldots$ between each adjacent structural element 40 is preferably about 20 μm to 1000 μm. The interval $d_1, d_2, \ldots$ between each adjacent structural element 40 is not necessarily required to be the same and may each be different provided the above-mentioned prescribed conditions are satisfied. For example, an aspect may be employed in which the interval $d_1, d_2, \ldots$ gradually becomes narrower moving in the downstream direction.

Furthermore, in the flow channel structure according to the present invention, in the case the axial direction of the upstream dilution flow channel or direction in which it extends is defined as the X direction and the widthwise direction of the dilution flow channel that intersects perpendicularly with this X direction is defined as the Y direction, although each structural element 40 is alternately extended from both sidewalls towards the center of the flow channel in an approximate Y direction (approximate +Y direction or approximate −Y direction) and the sidewalls are roughly at a right angle to the flow channel direction (X direction), this angle is not necessarily required to be 90°, but rather an effective configuration can be obtained even if inclined to a certain degree, and although there are no particular limitations thereon, more specifically, this angle is, for example, allowed to be within the range of about 30° to 150°, more preferably 40° to 140° and particularly preferably 80° to 100°. Moreover, the shape of the corner portion of each structural element 40 in the center of the flow channel is permitted to be rounded to a certain degree, and although there are no particular limitations thereon, there are cases in which rounding of, for example, R50 μm or less and more preferably R20 μm or less is permitted. However, in terms of obtaining uniform nano-sized lipid particles with a higher degree of controllability, these tolerances are preferably as small as possible. In addition, in the embodiments shown in FIGS. 2 and 3, although X direction, which is the axial direction of the upstream dilution flow channel in the flow channel structure or the direction in which it extends, is represented with a straight line for the sake of convenience, this X direction merely indicates the axial direction of the dilution flow channel, and in actuality, is not limited to this straight line, but rather may also, for example, be curved at a certain curvature. Furthermore, in such cases, the Y direction, which is the widthwise direction of the dilution flow channel that perpendicularly intersects this X direction, indicates a direction perpendicular to the X direction at a site of that unit length.

In addition, since the flow channel structure according to the present invention is a flow channel structure having a two-dimensional structure as previously described, the size in the direction of depth of the flow channel thereof (direction of paper thickness in FIGS. 2 and 3) is, for example, about 10 μm to 1000 μm and more preferably about 50 μm to 200 μm, although there are no particular limitations thereon.

Moreover, in the flow channel structure according to the present invention, the angle at which the first inlet channel 10 and the second inlet channel 20 join together may be a relatively obtuse angle, although there are no particular limitations thereon. Namely, in the formation of nano-sized lipid particles, since the flow rate of the merging fluids is quite fast, in the flow channel structure of the present invention, the merging angle of the first inlet channel 10 and the second inlet channel 20 does not have an extraordinarily large effect in terms of forming uniform nano-sized lipid particles. Although there are no particular limitations thereon, the merging angle is specifically within the range of about 10° to 180°.

In the flow channel structure according to the present invention for forming nano-sized lipid particles, either one of a first fluid that is introduced into the first inlet channel 10 or a second fluid that is introduced into the second inlet channel 2 is a lipid solution while the other is a dilution medium, and there are no particular limitations thereon. However, when the flow rates of the lipid solution and dilution medium used are compared in terms of forming nano-sized lipid particles, the flow rate of the dilution medium is typically faster. Thus, in the flow channel structure according to the present invention, the flow of the lipid solution on the upstream side of the dilution flow channel 30 immediately after the first inlet channel 10 and the second inlet channel 20 join together when viewed macroscopically flows downstream formed as a thin layer while the flow of the dilution medium flows downward formed as a thick layer. Consequently, in the case the second fluid introduced from the inlet channel (second inlet channel 20) side, located on the side of the sidewall (lower side in FIGS. 2 and 3) where the first structural element 40 of the bent flow channel site 50 is formed, is a lipid solution, the flow of the lipid solution collides considerably with the first structural element 40, thereby resulting in the risk of it being difficult to flow to the downward side as a result of being hindered by the thick flow layer of the dilution medium. Thus, an aspect is more preferably employed in which the first fluid introduced from the side of the inlet channel (first inlet channel 10) located on a sidewall on the opposite side from the sidewall (lower side in FIGS. 2 and 3) formed of the first structural element 40 of the bent flow channel site 50 is the lipid solution.

In addition, although there are no particular limitations on the widths of the first inlet channel 10 and the second inlet channel 20, since the flow channel width $y_0$ of the dilution flow channel 30 after they have joined together is typically about 100 μm to 200 μm as was previously described, these widths are each preferably set to about 50 μm to 400 μm and more preferably set to about 50 μm to 200 μm corresponding thereto.

Moreover, in the flow channel structure according to the present invention, if a distance $x_0$ from a confluence 31 of the first inlet channel 10 and the second inlet channel 20 to an upstream end 41 of the first structural element 40 is extremely long, or in other words, if excess time is required for the diluted fluid to reach the bent flow channel site 50 having the structural elements 40 disposed therein, there is a tendency for the particle diameter of the lipid particles formed to become large. Consequently, this distance (distance $x_0$) is preferably such that the dilution medium having a set flow rate passes through in 0.1 seconds or less. More specifically, in the case, for example, the set flow rate (total flow rate) of the dilution medium is 1 ml/min, the distance $x_0$ is preferably set to about 80 mm or less.

Moreover, in the flow channel structure according to the present invention, there are no particular limitations on the respective number of the first inlet channel 10 and the second inlet channel 20, a plurality of each can be provided. In particular, there are cases in which an aspect can be employed in which a plurality of inlet channels is preferably provided on the side where the dilution medium flows, which typically has a faster flow rate in comparison with the lipid solution. Namely, this is because, as a result of providing a plurality of inlet channels on the side where the dilution medium flows in this manner, even if the lipid solution flows at a relatively slow flow rate, there are cases in which the particle diameter of the formed lipid particles and the standard deviation thereof can be made to be smaller values with favorable controllability.

Figure 18:
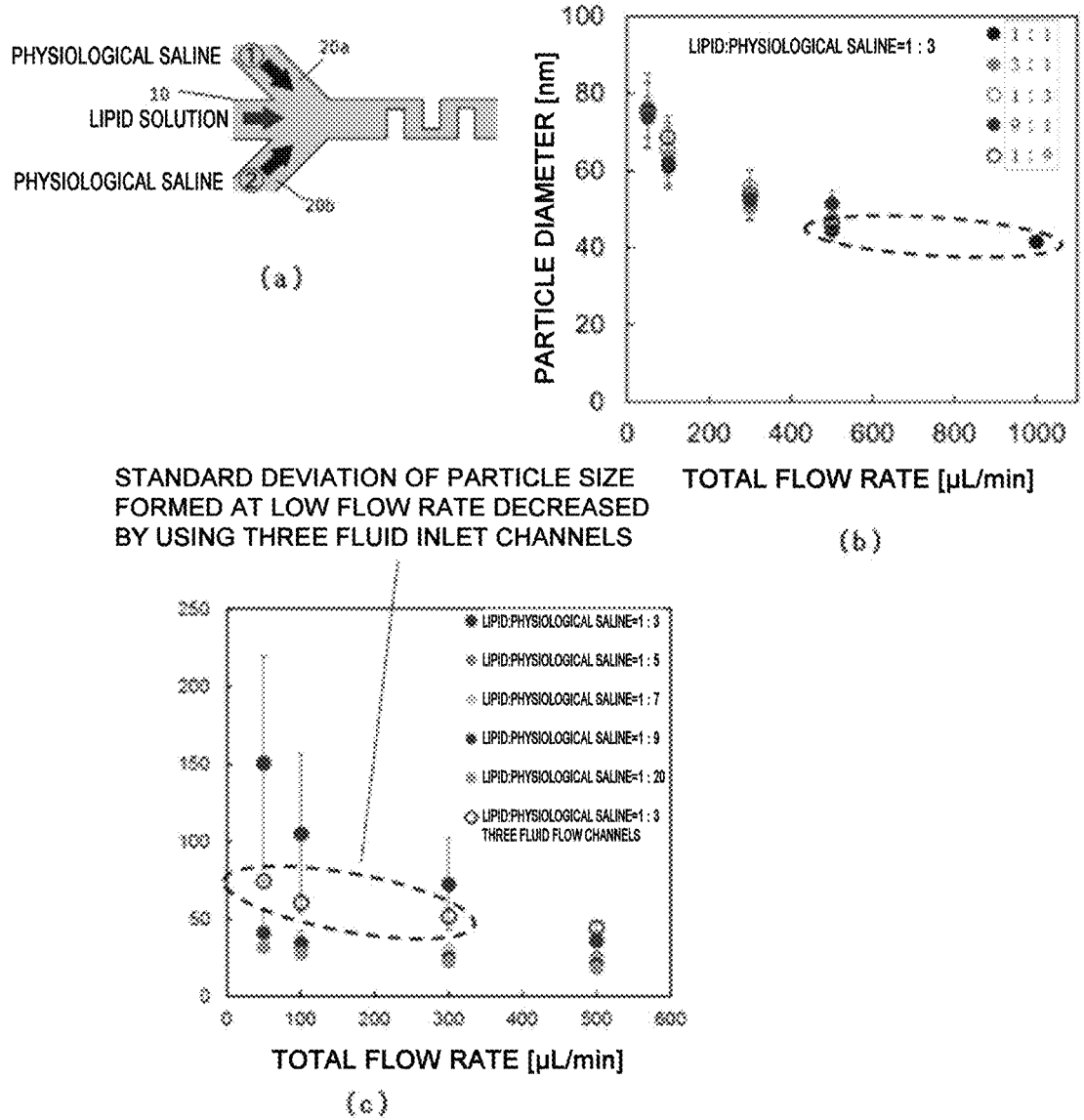
FIG. 18(a) is a drawing schematically showing the structure of a flow channel structure used in an example.
FIGS. 18(b) and 18(c) are graphs indicating the relationship between the resulting structure and the particle diameter of formed lipid particles.

Although there are no particular limitations thereon, FIG. 18 shows an example of an embodiment having such a plurality of second inlet channels (and/or first inlet channels) of the flow channel structure according to the present invention in which the structure has a single inlet channel for the first inlet channel 10, which introduces a lipid solution as a first fluid, and two inlet channels 20*a* and 20*b* for the second inlet channel 20, which introduces the dilution medium as a second fluid. In the example shown in FIG. 18, although the two second inlet channels 20*a* and 20*b* respectively join together from both sides at a relatively acute angle with respect to the central first inlet channel 10, even in a form having a plurality of second inlet channels (and/or first inlet channels) in this manner, there are no particular limitations on the angle at which the first inlet channel and second inlet channels join together and may join together at a relatively obtuse angle as previously described.

In addition, in a form having a plurality of second inlet channels (and/or first inlet channels) in this manner, there are no particular limitations on the flow rate ratio of the fluids flowing through each of the plurality of second inlet channels (and/or first inlet channels), or in other words, there are no particular limitations on the flow rate ratio of the dilution medium respectively flowing through the two second inlet channels 20*a* and 20*b* in the case of the example shown in FIG. 18, for example. Namely, since the flow channel structure according to the present invention functions effectively even if each fluid is allowed to flow from that in which there is only one each of the first and second inlet channels, in the case of having a plurality of each inlet channel, the mutual flow rate ratio of the same type of a plurality of inlet channels can be arbitrary and that flow rate ratio is not limited to 1:1, or in other words, an aspect in which equal amounts each flow from a plurality of inlet channels, but rather can be suitably altered as necessary in consideration of the particle diameter and so forth of the lipid particles to be obtained. Furthermore, if the configuration of the bent flow channel site 50 having the flow channel structure according to the present invention employs a preferable aspect, as is indicated in the examples to be subsequently described, if the flow rate ratio of the dilution medium is within the range of about 1:1 to 1:10 in the case there are a plurality (two) of second inlet channels introducing the dilution medium, there are is no large effect on particle diameter of the formed lipid particles, and the particle diameter and standard deviation thereof of the formed lipid particles can be made to be of smaller values with favorable controllability within this range.

Figure 25:
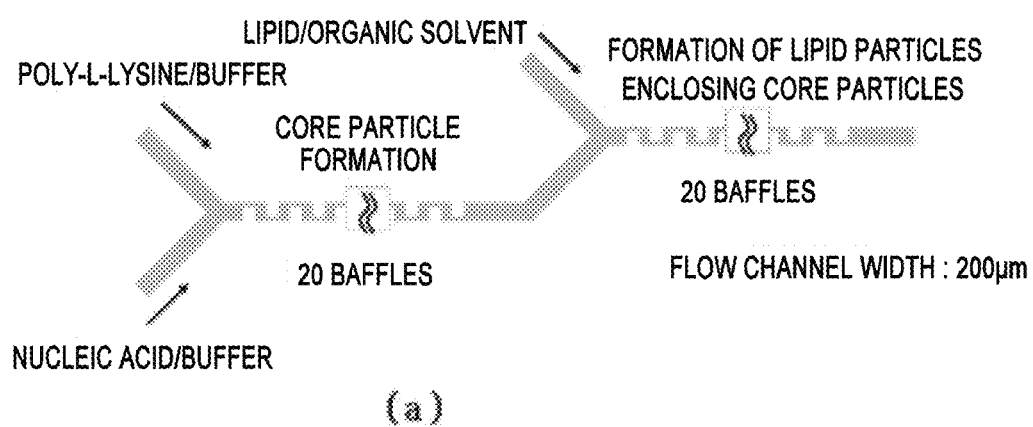
FIG. 25(a) is a drawing schematically showing the structure of a flow channel structure used in an example.
FIG. 25(b) is a graph indicating the relationship between particle diameter and flow rate of lipid particles enclosing a nucleic acid-polycation complex obtained as a result thereof.
Figure 25:
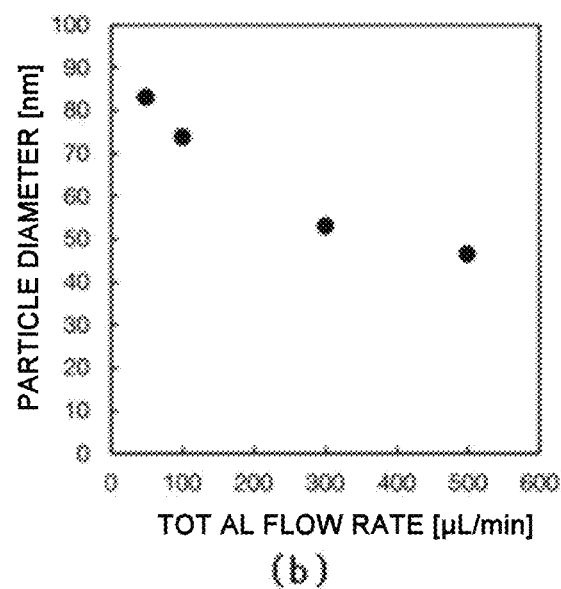

Moreover, although the flow channel structure according to the present invention is a flow channel structure for forming nano-sized lipid particles or micelles of amphipathic substances such as amphipathic polymers as was previously described, in the case of enclosing a core particle demonstrating a capsule structure similar to the bent flow channel site, for example, as a contained physiologically active substance like that to be subsequently described within this nano-sized lipid particle or micelle of an amphipathic substance such as an amphipathic polymer, a flow channel having a similar structure to the flow channel structure having a bent flow channel site according to the present invention as previously described can be provided as a flow channel for a pretreatment process for forming this core particle, and the second inlet channel (or first inlet channel) can be composed by connecting to the downstream side of this flow channel for a pretreatment process. Furthermore, the connected inlet channel is inherently a flow channel used as the side where the dilution medium is introduced. FIG. 25(*a*) schematically shows this type of configuration, and as indicated in the drawing, the overall flow channel has a form such that bent flow channel sites have been combined in multiple stages. As a result of using this aspect of a structure having a multistage bent flow channel site in this manner, the inclusion of a physiologically active substance as a core particle demonstrating a capsule structure within a nano-sized lipid particle or micelle of an amphipathic substance such as an amphipathic polymer can be prepared by a series of procedures. Furthermore, the bent flow channel site for a pretreatment process and the bent flow channel site for the main process of forming a lipid particle or micelle are only the same in the sense that they both satisfy the above-mentioned regulatory conditions, or in other words, in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$, at least two or more structural elements 40, which define flow channel width of the dilution flow channel by alternately protruding from both side surfaces of the dilution flow channel in opposition to the Y direction towards the center of the flow channel at a fixed height $h_1, h_2, \ldots$ of $1/2y_0$ or more and less than $1y_0$ in an approximate Y direction (approximate +Y direction or approximate −Y direction) and at a fixed width $x_1, x_2, \ldots$ in the X direction, are provided at fixed intervals $d_1, d_2, \ldots$, and are not limited to an aspect in which both have completely identical structures. The arrangement, number and size of these structural elements along with the flow speed conditions of the fluid can be set to conditions corresponding to each site corresponding to the prescribed particle diameter to be formed in each flow channel site, the material used and so forth. Furthermore, conditions such as the arrangement, number and size of the structural elements, the width of the dilution flow channel and the number of inlet channels used in the flow channel structure used as a flow channel for a pretreatment process are the same as those explained relating to the previously described original flow channel structure for forming lipid particles or micelles, and an explanation thereof has been omitted.

Next, an explanation is provided of the lipid particle or micelle formation method according to the present invention. The lipid particle formation method according to the present invention is characterized in that, a lipid solution or amphipathic substance solution is introduced from one of the first inlet channel 10 and the second inlet channel 20 of a flow channel structure while a dilution solvent is introduced from the other inlet channel at a total flow rate of 1 µl/min to 100 ml/min using this flow channel structure.

According to this method, lipid particles or micelles of an amphipathic substance can be prepared of a desired size, and more specifically, an arbitrary size within the range of a particle diameter of, for example, about 10 nm to 100 nm, and the produced lipid particles or micelles can be preferably used, for example, as nanocarriers for an efficient drug delivery system (DDS).

Although as previously described, the flow channel structure used in the lipid particle formation method of the present invention is characterized in that, by making the number of structural elements 40, the height $h_1$, $h_2$, ... (length in the Y direction) of each structural element 40, the width $x_1$, $x_2$, ... (length in the X direction) of each structural element 40 and the interval $d_1$, $d_2$, ... between each adjacent structural element 40 to be within prescribed ranges, the range of particle diameter of the lipid particles formed can be changed to be within a prescribed range, and by further adjusting the flow rate and dilution factor of a feedstock solution, desired nano-sized lipid particles can be formed with favorable controllability.

Furthermore, in the case of using a conventional microdevice, although lipid particles of a particle diameter of about 20 nm, which was theoretically the smallest size at which lipid particles were able to be formed, were unable to be formed unless the solution was fed at a considerably high flow rate of, for example, about 5 ml/min, in the present invention, use of the flow channel structure according to the present invention as previously described makes it possible to prepared lipid particles having a particle diameter of about 20 nm with favorable controllability even if solution is fed at a lower flow rate of, for example, 500 µl/min.

In the lipid particle formation method of the present invention, although the total flow rate of the lipid solution and dilution solvent fed to the above-mentioned flow channel structure is suitably adjusted within a range of 1 µl/min to 100 ml/min as previously described corresponding to the size of the lipid particles to be formed and differences in the configuration of the flow channel structure, from the viewpoint of controllability of particle diameter, the total flow rate is more preferably within the range of 50 µl/min to 500 µl/min.

There are no particular limitations on the compositions of the lipid solution and dilution medium used in the lipid particle formation method of the present invention or on the resulting dilution factors thereof. In principle, the lipid particle or micelle formation method of the present invention forms lipid particles, including liposomes, or micelles of an amphipathic substance by adding a solution obtained by dissolving a lipid or amphipathic substance in a water-miscible organic solvent under warming conditions as necessary to an aqueous solution (dilution medium) and diluting therewith, and a conventionally known composition and the like can be used in this method.

Although there are no particular limitations thereon, one or two or more lipids, such as soybean lecithin, hydrogenated soybean lecithin, egg yolk lecithin, phosphatidylcholines, phosphatidylserines, phosphatidylethanolamines, phosphatidylinositols, phosphasphingomyelins, phosphatidic acids, long chain alkyl phosphates, gangliosides, glycolipids, phosphatidylglycerols or sterols, can be used for the lipid component contained in the lipid solution. In an aspect in which lipid particles are used as carriers for a drug delivery system (DDS), a preferable example thereof consists of the use of a combination of phospholipid and cholesterol, as lipids constituting lipid particles (such as liposomes), and particularly, a combination of a phosphatidylcholine, which is a type of phospholipid, and cholesterol.

In addition, although there are no particular limitations thereon, examples of amphipathic substances include amphipathic polymer compounds such as amphipathic block copolymers in the manner of polystyrene-polyethylene oxide block copolymer, polyethylene oxide-polypropylene oxide block copolymer, polylactic acid-polyethylene glycol copolymer and polycaprolactone-polyethylene glycol copolymer.

Although there are no particular limitations thereon, organic solvents that are miscible in water, such as alcohols, ethers, esters, ketones or acetals, and particularly, alcohols such as ethanol, t-butanol, 1-propanol, 2-propanol or 2-butoxyethanol, are preferably used for the water-miscible organic solvent used to prepare the lipid solution by dissolving a lipid as previously described. In addition, although similar substances can be used for the water-miscible organic solvent used to prepare the amphipathic substance solution, preferable examples thereof include ethers such as tetrahydrofuran and chloroform.

On the other hand, an aqueous solution such as physiological saline, phosphate buffer solution, acetate buffer solution, or citrate buffer solution, having water or basically having water as the main component thereof, is suitably used for the dilution medium corresponding to the application of the lipid particles to be formed.

In addition, a physiologically active substance can be incorporated in the lipid particle or micelle as is commonly known corresponding to the application of the resulting lipid particle or micelle. Although there are no particular limitations thereon, examples thereof include drugs, physiological active substances, and cosmetics such as an anticancer drug, antioxidant, antimicrobial agent, anti-inflammatory agent, vitamin, hemoglobin, DNA, RNA, peptide, protein, vaccine, hair growth agent, moisturizer, pigment, whitening agent or colorant. These additives can be contained in the aqueous phase of the lipid particle or micelle formed by incorporating in the above-mentioned dilution medium provided they are water-soluble. In addition, these additives can be incorporated in the lipid membrane of the lipid particle provided they are lipid-soluble. Moreover, a drug, physiologically active substance or cosmetic and the like, for example, can be incorporated in a lipid particle or micelle formed according to the present invention in the form of a particle (core particle) in which these additives are dispersed in the aqueous phase.

In addition, the surface of a lipid particle can be modified with a functional group and the like as is commonly known in the art. Modification by a functional group can be realized by preliminarily bonding a functional group to a phospholipid and the like or by bonding the functional group after having formed the lipid particle. Furthermore, there are no particular limitations on the concentration of water-miscible organic solvent in the above-mentioned lipid solution or on the blending ratio of the dilution medium used to dilute the lipid solution provided it is within a suitable range dependent on the lipid composition or lipid concentration so that a lipid particle (liposome) is formed as is commonly known in the art.

Furthermore, in the lipid particle of micelle formation method according to the present invention, since a lipid solution or amphipathic substance is diluted with a dilution medium using the flow channel structure as previously described, there are no particular limitations thereon, and although influenced to a certain degree by the type of lipid or amphipathic substance and the type of water-miscible organic solvent used, more specifically, the ratio of the flow rate of the lipid solution or amphipathic substance solution to the flow rate of the dilution medium is about 1:1 to 1:50 and more preferably about 1:3 to 1:10 in terms of obtaining favorable dispersion efficiency.

EXAMPLES

Although the following provides a more detailed explanation of the present invention based on examples thereof, the present invention is not limited in any way to these examples.

Example 1

The effect of the number of structural elements 40 required to produce desired nano-sized lipid particles in a flow channel structure having the basic structure shown in FIG. 2 was investigated.

Figure 4:
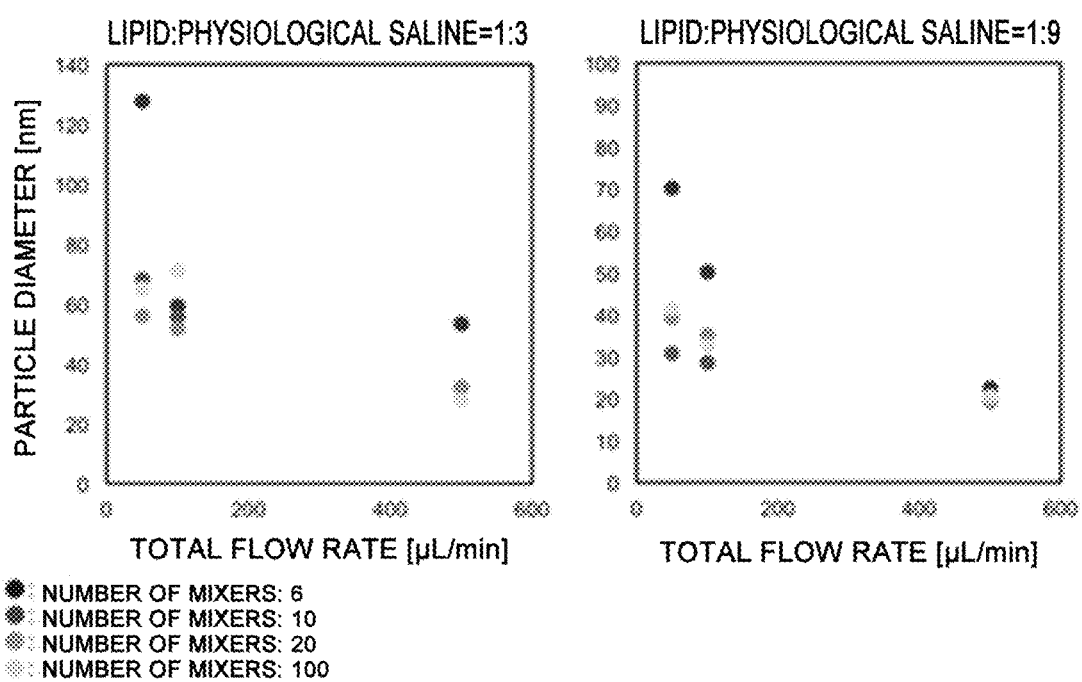
FIG. 4 is a graph indicating the relationship between the number of structural elements and the particle diameter of formed lipid particles of a flow channel structure obtained in an example.

Flow channel structures were fabricated in which the number of structural elements 40 was 6, 10, 20 and 100, respectively while using the same parameters of flow channel width $y_0$=200 μm, height $h_1$, $h_2$, . . . (length in Y direction) of each structural element 40=150 μm, width $x_1$, $x_2$, . . . (length in X direction) of each structural element 40=100 μm and interval $d_1$, $d_2$, . . . between each adjacent structural element 40=100 μm. A lipid solution (10 mg/ml of phosphatidylcholine solution in ethanol) was introduced from the first inlet channel 10 of these flow channel structures and physiological saline was introduced from the second inlet channel at a flow rate ratio of 1:3 or 1:9 while adjusting to a prescribed total flow rate, followed by forming lipid particles and investigating the particle diameter of the resulting lipid particles. The results are shown in FIG. 4. As shown in FIG. 4, although nano-sized lipid particles were able to be formed under any of the conditions, particles of a target size within the range of 20 nm to 100 nm were able to be formed with favorable controllability if the number of structural elements 40 was 10 or more in particular.

Example 2

The interval $d_1$, $d_2$, . . . between adjacent structural elements 40 required to produce desired nano-sized lipid particles in a flow channel structure having the basic structure shown in FIG. 2 was investigated.

Figure 5:
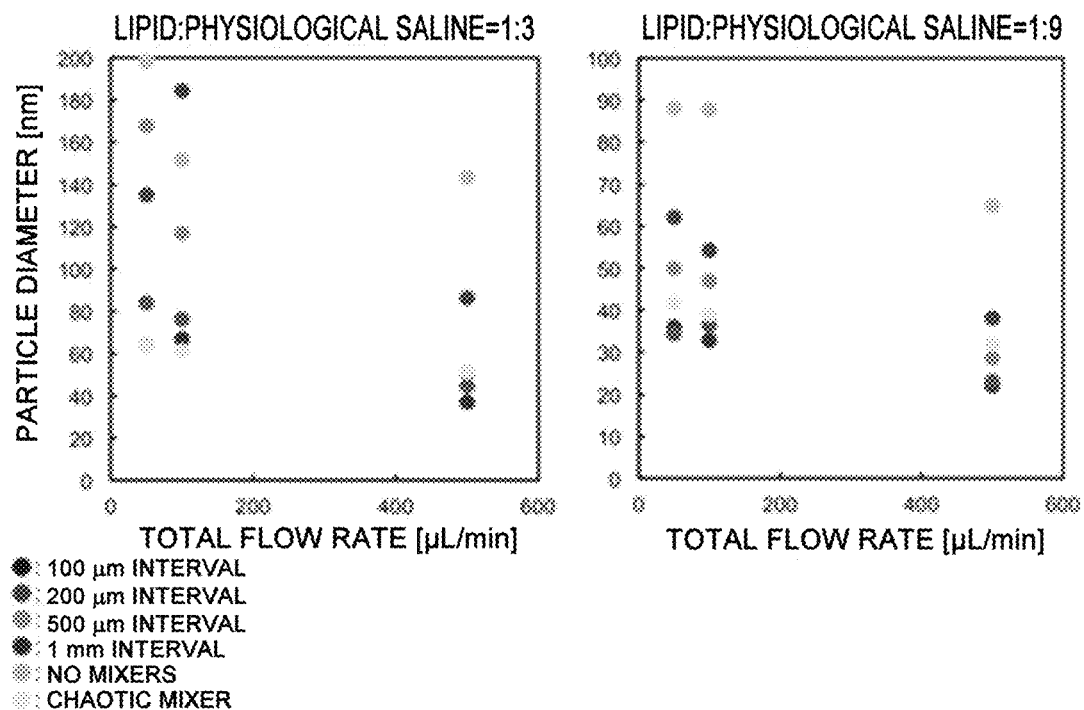
FIG. 5 is a graph indicating the relationship between the interval between structural elements and the particle diameter of formed lipid particles of a flow channel structure obtained in an example.

Flow channel structures were fabricated in which the interval $d_1$, $d_2$, . . . between adjacent structural elements 40 was 100 μm, 200 μm, 500 μm or 1 mm, respectively, while using the same parameters of flow channel width $y_0$=200 μm, number of structural elements 40=100, height $h_1$, $h_2$, . . . (length in Y direction) of each structural element 40=150 μm and width $x_1$, $x_2$, . . . (length in X direction) of each structural element 40=100 μm. A lipid solution (10 mg/ml of phosphatidylcholine solution in ethanol) was introduced from the first inlet channel 10 of these flow channel structures and physiological saline was introduced from the second inlet channel at a flow rate ratio of 1:3 or 1:9 while adjusting to a prescribed total flow rate, followed by forming lipid particles and investigating the particle diameter of the resulting lipid particles. Furthermore, a similar test was carried out in the absence of structural elements 40 and using a conventionally known chaotic mixer in a flow channel structure of the same flow channel width for reference purposes. Furthermore, the same chaotic mixer in accordance with the contents described in the above-mentioned NPL 1 (chaotic mixer having a width of 50 μm and depth of 31 μm arranged for 69 cycles in a flow channel having a diameter of 200 μm) was fabricated and used in the above-mentioned test (the description of the relevant portion of NPL 1 is included in the present description in connection therewith). The results are shown in FIG. 5. As shown in FIG. 5, although nano-sized lipid particles were able to be formed under any of the conditions, particles of a target size within the range of 10 nm to 100 nm were able to be formed with favorable controllability if the interval $d_1$, $d_2$, . . . between adjacent structural elements 40 was 500 μm or less in particular.

Example 3

The effect of height $h_1$, $h_2$, . . . (length in Y direction) of each structural element 40 required to produce desired nano-sized lipid particles in a flow channel structure having the basic structure shown in FIG. 2 was investigated.

Figure 6:
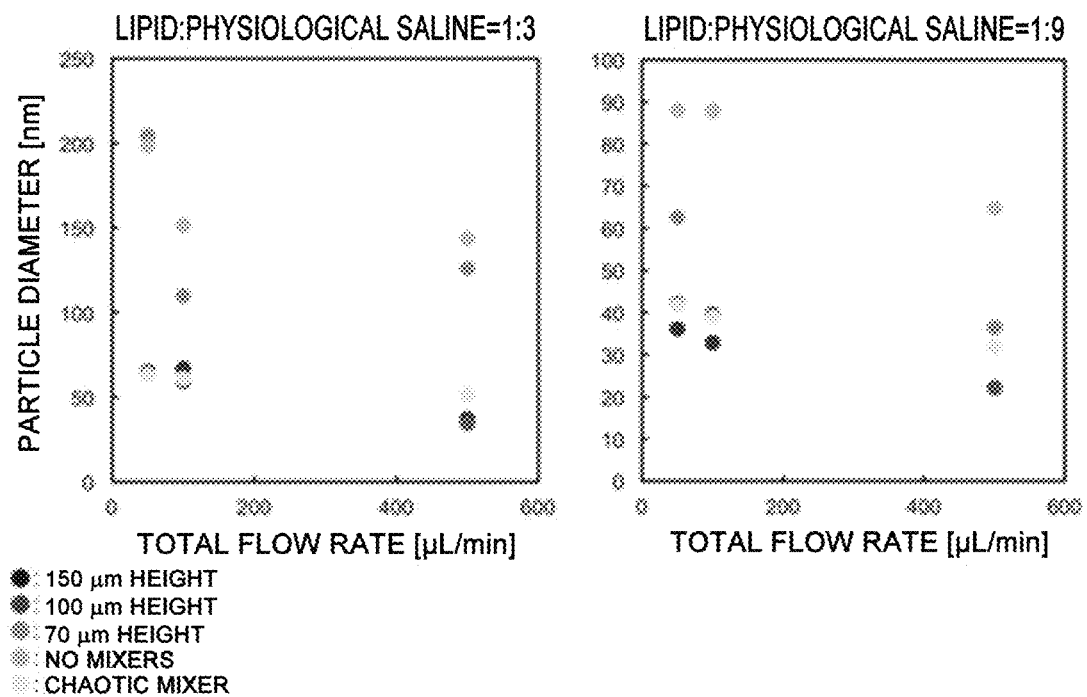
FIG. 6 is a graph indicating the relationship between the height of structural elements and the particle diameter of formed lipid particles of a flow channel structure obtained in an example.

Flow channel structures were fabricated in which the height $h_1$, $h_2$, . . . (length in Y direction) of each structural element 40 was 70 μm, 100 μm or 150 μm while using the same parameters of flow channel width $y_0$=200 μm, number of structural elements 40=100, width $x_1$, $x_2$, . . . (length in X direction) of each structural element 4=100 μm, and interval $d_1$, $d_2$, . . . between adjacent structural elements 40=100 μm. A lipid solution (10 mg/ml of phosphatidylcholine solution in ethanol) was introduced from the first inlet channel 10 of these flow channel structures and physiological saline was introduced from the second inlet channel at a flow rate ratio of 1:3 or 1:9 while adjusting to a prescribed total flow rate, followed by forming lipid particles and investigating the particle diameter of the resulting lipid particles. Furthermore, a similar test was carried out in the absence of structural elements 40 and using a conventionally known chaotic mixer (same as that used in Example 2) in a flow channel structure of the same flow channel width for reference purposes. The results are shown in FIG. 6. As shown in FIG. 6, particles of a target size within the range of 10 nm to 100 nm were able to be formed with favorable controllability if the height $h_1$, $h_2$, . . . (length in Y direction) of each structural element 40 was 100 μm.

Example 4

The effect of width $x_1$, $x_2$, . . . (length in X direction) of each structural element 40 required to produce desired nano-sized lipid particles in a flow channel structure having the basic structure shown in FIG. 2 was investigated.

Figure 7:
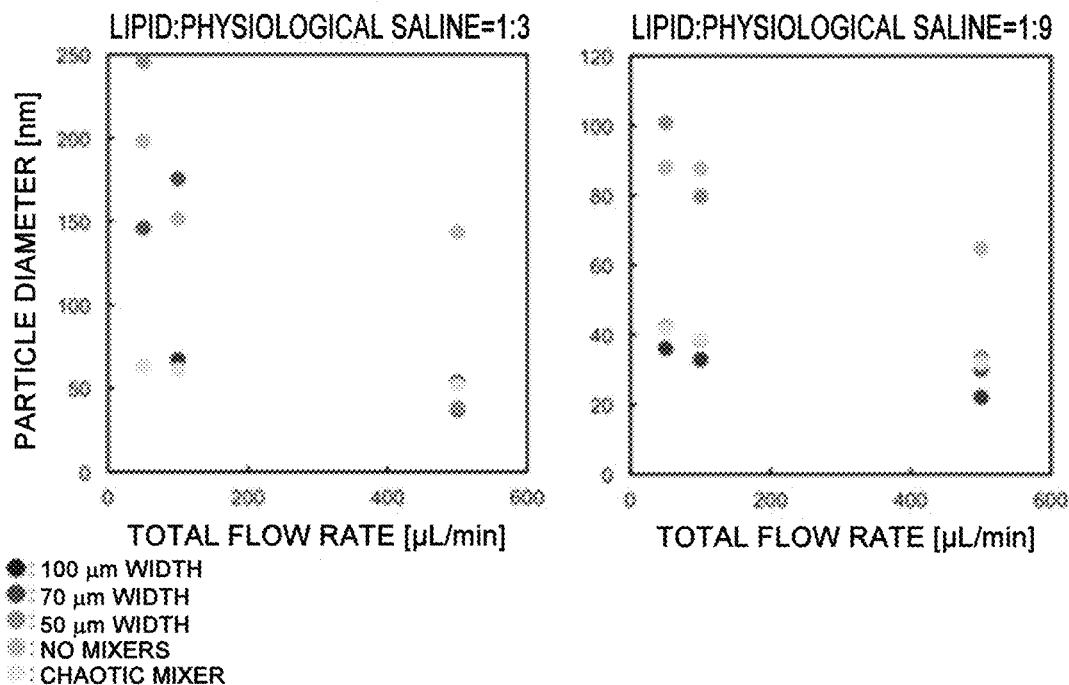
FIG. 7 is a graph indicating the relationship between the width of structural elements and the particle diameter of formed lipid particles of a flow channel structure obtained in an example.

Flow channel structures were fabricated in which the width . . . (length in X direction) of each structural element 40 was 50 μm, 70 μm or 100 μm while using the same parameters of flow channel width $y_0$=200 μm, number of structural elements 40=100, height $h_1$, $h_2$, . . . (length in Y direction) of each structural element 40=150 μm and interval $d_1$, $d_2$, between adjacent structural elements 40=100 μm. A lipid solution (10 mg/ml of phosphatidylcholine solution in ethanol) was introduced from the first inlet channel 10 of these flow channel structures and physiological saline was introduced from the second inlet channel at a flow rate ratio of 1:3 or 1:9 while adjusting to a prescribed total flow rate, followed by forming lipid particles and investigating the particle diameter of the resulting lipid particles. Furthermore, a similar test was carried out in the absence of structural elements 40 and using a conventionally known chaotic mixer (same as that used in Example 2) in a flow channel structure of the same flow channel width for reference purposes. The results are shown in FIG. 7. As shown in FIG. 7, although nano-sized lipid particles were able to be formed under any of the conditions, particles of a target size within the range of 10 nm to 100 nm were able to be formed with favorable controllability if the width $x_1$, $x_2$, . . . (length in X direction) of each structural element 40 was 100 μm in particular.

Example 5

Figure 9:
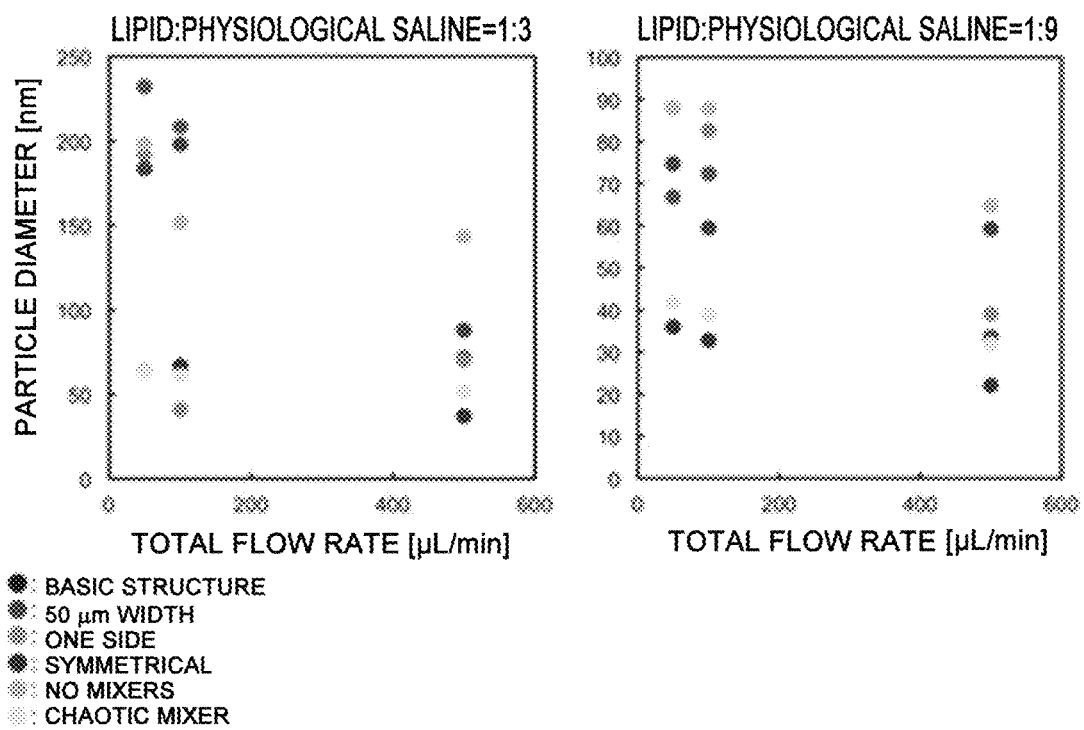
FIG. 9 is a graph indicating the relationship between the arrangement of structural elements and the particle diameter of formed lipid particles of a flow channel structure obtained in an example.

A flow channel structure having the basic structure according to the present invention as shown in FIG. 8 (flow channel width $y_0$=200 μm, number of structural elements 40=100, height $h_1$, $h_2$, . . . (length in Y direction) of each structural element 40=150 μm, width $x_1$, $x_2$ (length in X direction) of each structural element 40=100 μm and interval $d_1$, $d_2$, . . . between adjacent structural elements 40=100 μm) along with flow channel structures having (1) a shape such that a single structural element 40 of the same height but larger width is provided on one sidewall, (2) a shape such that a plurality of structural elements 40 of the same height are provided on only one sidewall, and (3) a shape such that a plurality of structural elements 40 are provided on both sidewalls but are each arranged symmetrically and the height of each structural element is half, were respectively fabricated followed by investigating the effect of the structural elements in terms of producing desired nano-sized lipid particles. The results are shown in FIG. 9. As shown in FIG. 9, only the flow channel structure having the basic structure according to the present invention was able to form lipid particles of a target size with favorable controllability.

Example 6

Figure 10:
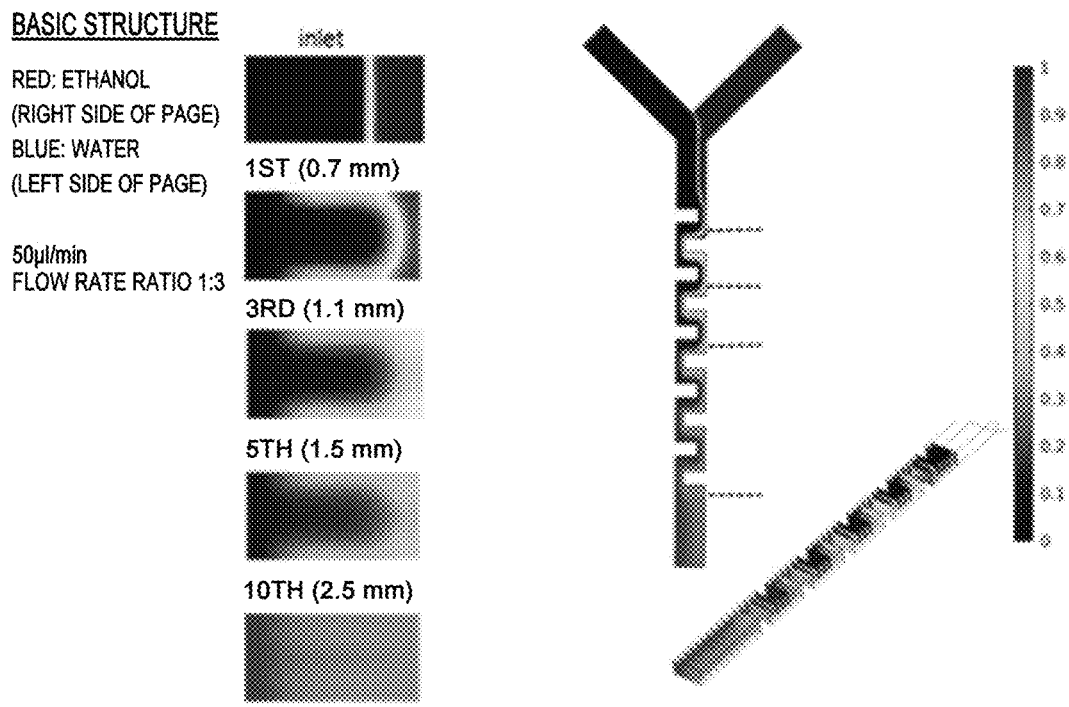
FIG. 10 indicates the results of a simulation showing the effects of structural elements in a flow channel structure used in an example.

In order to simulate the diluted state of a lipid solution in a flow channel structure having the basic structure according to the present invention, ethanol, which is a water-miscible organic solvent of the lipid solution, and water as a dilution solvent, were allowed to flow into the flow channel structure at a flow rate ratio of 1:3 and total flow rate of 50 μl/min followed by simulating the flow thereof with the COMSOL Multiphysics general-purpose physics simulation software. The results are shown in FIG. 10. As shown in FIG. 10, the lipid solution was diluted and dispersed due to the presence of the structural elements, and dispersion was confirmed to proceed considerably uniformly when the number thereof was 10 in particular.

Example 7

In order to investigate the effect of the length of distance $x_0$ from the confluence 31 of the first inlet channel 10 and the second inlet channel 20 to the upstream end 41 of the first structural element 40 on the particle diameter of lipid particles, flow channel structures were fabricated while respectively changing that distance $x_0$ to 30 mm, 50 mm, 65 mm, 80 mm or 100 mm in a flow channel structures having the basic structure according to the present invention. Furthermore, the parameters of flow channel width $y_0$=200 μm, number of structural elements 40=100, height $h_1$, $h_2$, . . . (length in Y direction) of each structural element 40=150 μm, width $x_1$, $x_2$ (length in X direction) of each structural element 40=100 μm and interval $d_1$, $d_2$, . . . between adjacent structural elements 40=100 μm of these flow channel structures were the same for each flow channel structure.

Figure 11:
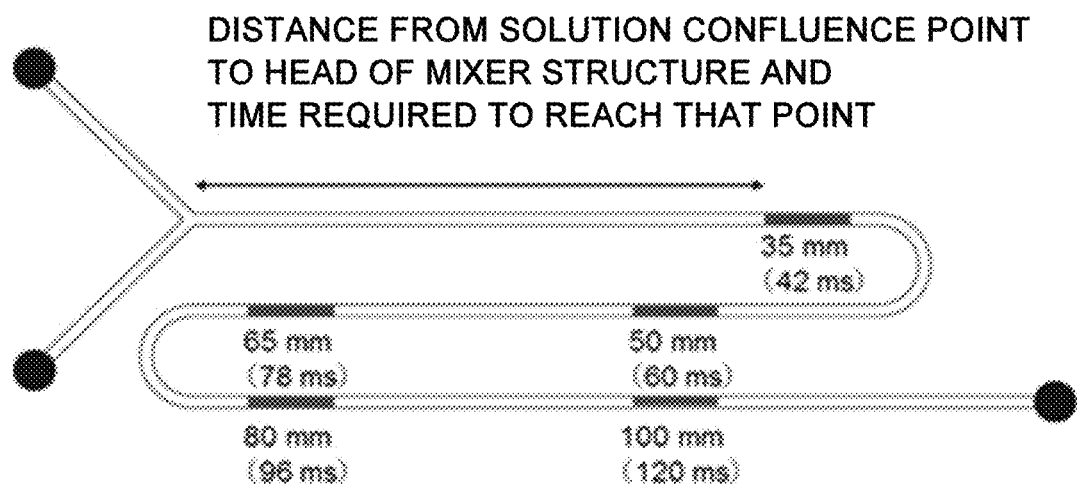
FIG. 11 is a drawing explaining the distance from a solution confluence point to the upstream end of a first structural element in a flow channel structure used in an example.
Figure 12:
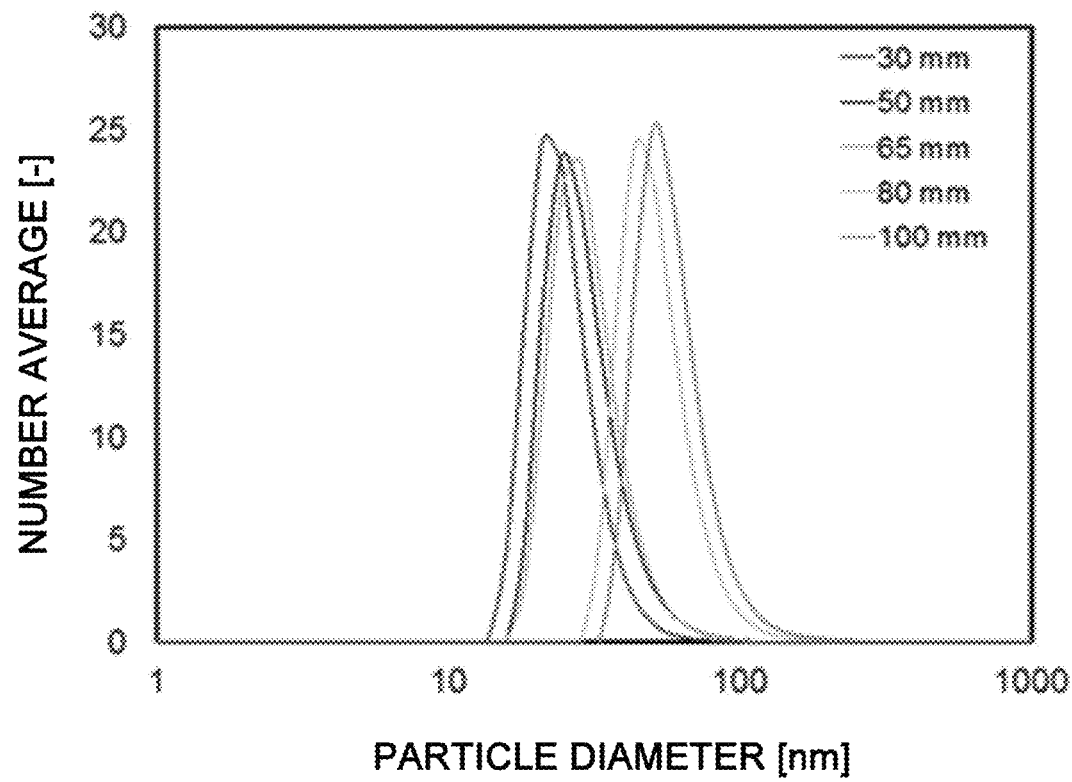
FIG. 12 is a graph indicating the relationship between the distance from a solution confluence point to the upstream end of a first structural element and particle diameter of a resulting lipid particle in a flow channel structure used in an example.

A 10 mg/ml phospholipid/ethanol solution as lipid solution was allowed to flow in at a flow rate of 0.1 ml/min and physiological saline as a dilution medium was allowed to flow in at a flow rate of 0.9 ml/min (total flow rate: 1.0 ml/min) followed by a comparison of particle diameter of the formed lipid particles. Furthermore, FIG. 11 schematically indicates the relationship between distance from the confluence 31 and time required to reach that point in the case of having allowed the lipid solution and dilution solvent to flow at this total flow rate. The results obtained are shown in FIG. 12. As shown in FIG. 12, the particle diameter of the resulting lipid particles ended up increasing if the distance $x_0$ was 80 mm or more (transit time: about 0.1 seconds or more). On the other hand, favorable particle diameter was obtained if the distance $x_0$ was 65 mm or less (transit time: about 0.08 seconds or less).

Example 8

Figure 13:
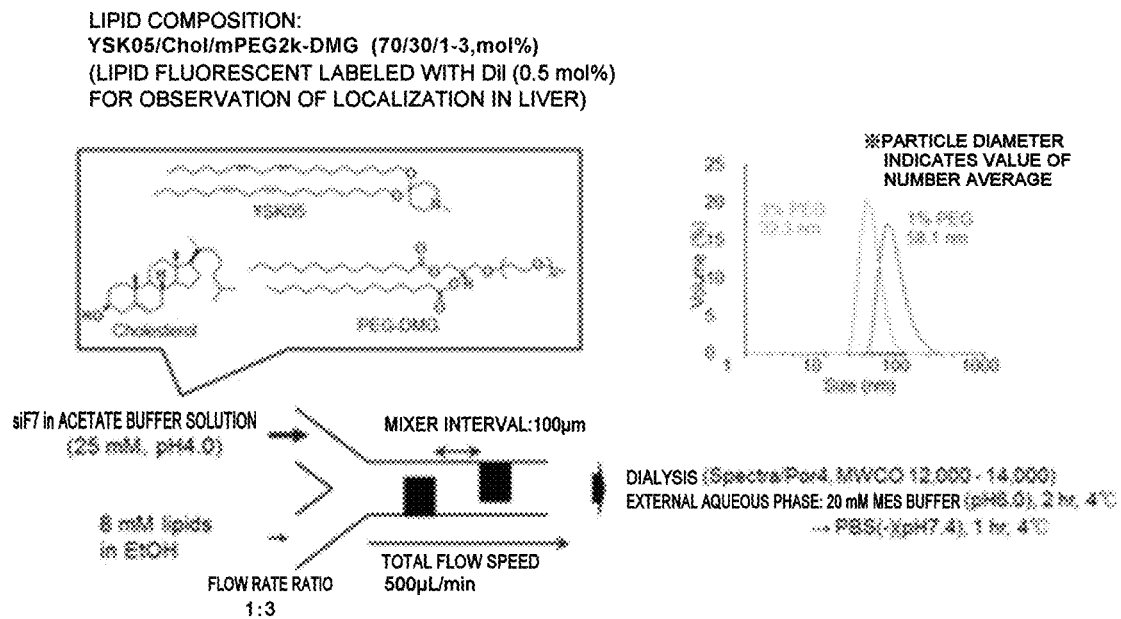
FIG. 13 is a drawing explaining an overview of an evaluation of an in vivo experiment on nano-sized lipid particles obtained according to the lipid particle formation method according to the present invention.

Lipid particles composed of a pH-responsive cationic lipid (YSK05), cholesterol, polyethylene glycol lipid and siRNA were attempted to be produced by allowing lipid solutions having a lipid composition consisting of a pH responsive cationic lipid (YSK05), cholesterol and polyethylene glycol lipid (ratio of YSK05/cholesterol/mPEG2k-DMG=70/30/1-3 (mol %)) (8 mM lipid concentration in ethanol) and an siRNA solution as a dilution medium (25 mM acetate buffer, pH 4.0) into a flow channel structure having the basic structure according to the present invention (flow channel width $y_0$=200 μm, number of structural elements 40=100, height $h_1$, $h_2$, . . . (length in Y direction) of each structural element 40=150 μm, width $x_1$, $x_2$, (length in X direction) of each structural element 40=100 μm and interval $d_1$, $d_2$, . . . between adjacent structural elements 40=100 μm) at a flow rate of ratio 1:3 and total flow speed of 500 μl/min. As a result, as shown in FIG. 13, lipid nanoparticles of a highly uniform size and having a particle diameter of 100 nm or less were able to be confirmed to be formed.

Figure 14:
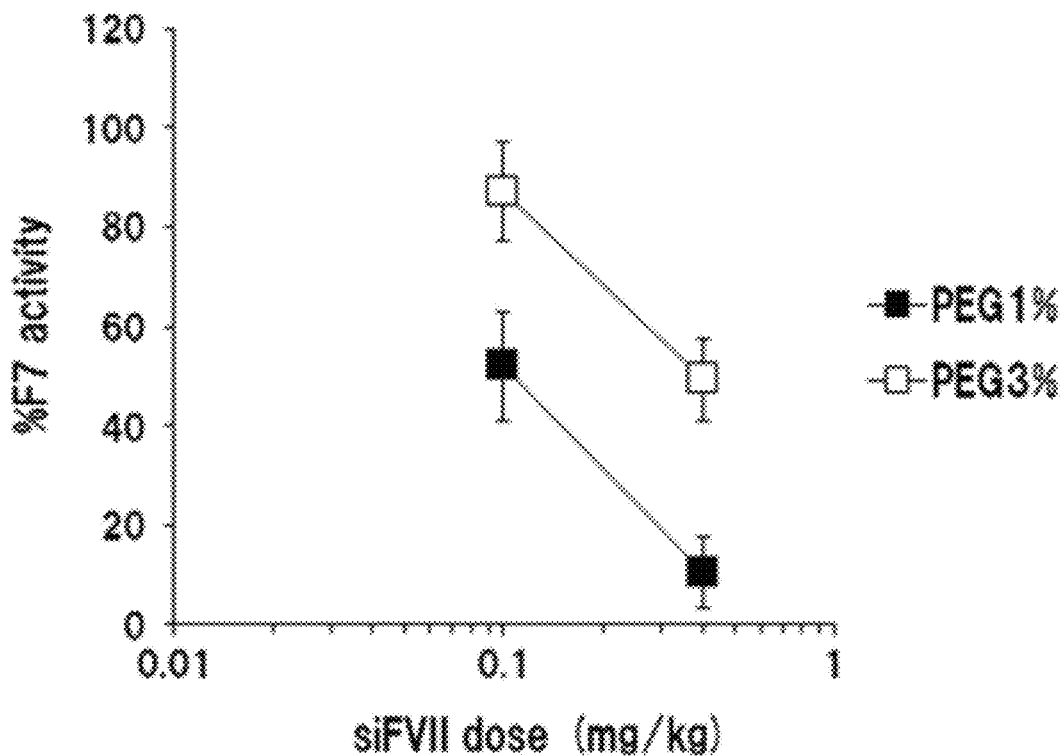
FIG. 14 is a graph indicating gene knockdown activity in lipid particle liver parenchymal cells in an in vivo experiment using nano-sized lipid particles obtained according to the lipid particle formation method according to the present invention.
Figure 15:
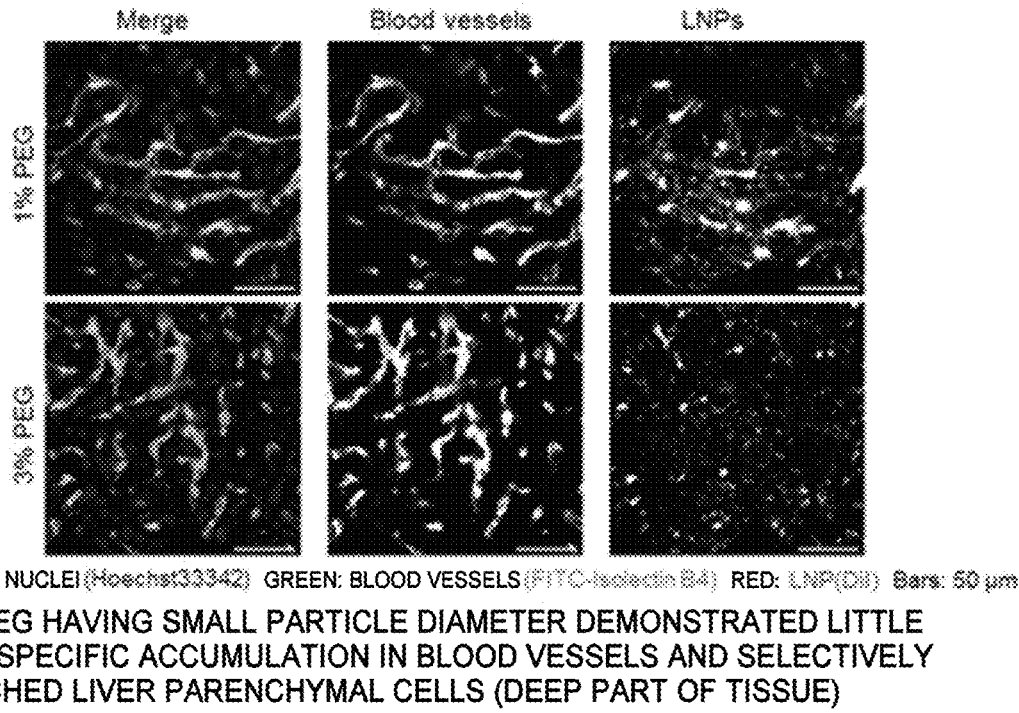
FIG. 15 depicts photomicrographs indicating the results of observing the interior of the liver in an in vivo experiment using nano-sized lipid particles obtained according to the lipid particle formation method according to the present invention.

Each of the produced lipid nanoparticles was administered intravenously to 4-week-old ICR mice at a ratio of 0.1 mg (siRNA)/kg (body weight) or 0.4 mg (siRNA)/kg (body weight) followed by observing gene knockdown activity in liver parenchymal cells and localization of the administered drugs in the liver. Gene knockdown activity in liver parenchymal cells was determined by collecting blood 24 hours after intravenous administration and investigating factor VII (F7) activity in plasma. Localization in the liver was observed by observing each site in the liver 30 minutes after intravenous administration with a confocal laser scanning microscope. Furthermore, lipid nanoparticles in which the lipid was fluorescent-labeled with DiI (0.5 mol %) were used for the lipid particles used to observe localization in the liver. The results obtained are shown in FIGS. 14 and 15. As shown in FIG. 14, lipid particles produced using the flow channel structure according to the present invention favorably demonstrated dose-dependent gene knockdown activity in vivo, and 1% PEG in particular, having a large particle diameter, exhibited high activity (about 3-fold). In addition, as shown in FIG. 15, lipid particles produced using the flow channel structure according to the present invention demonstrated a favorable drug delivery action in vivo, and 3% PEG in particular, having a small particle diameter, demonstrated little non-specific accumulation in the blood and selectively reached the liver parenchymal cells (deep tissue).

Example 9

The effect of flow channel width $y_0$ required to produce lipid nanoparticles of a desired size in the flow channel structure according to the present invention was investigated.

As shown in FIG. 16(a), flow channel structures were respectively prepared consisting of the flow channel structure having the basic structure according to the present invention (flow channel width $y_0$=200 μm, number of structural elements 40=100, height $h_1$, $h_2$, . . . (length in Y direction) of each structural element 40=150 μm, width $x_1$, $x_2$ (length in X direction)=100 μm and interval $d_1$, $d_2$, . . . between adjacent structural elements 40=100 μm), along with (1) a flow channel structure in which flow channel width $y_0$=400 μm, number of structural elements 40=100, height $h_1$, $h_2$, . . . (length in Y direction) of each structural element 40=300 μm, width $x_1$, $x_2$ (length in X direction)=100 μm and interval $d_1$, $d_2$, . . . between adjacent structural elements 40=100 μm, with the flow channel width being wider than the flow channel structure of the above-mentioned basic structure, but the ratio of the flow channel width $y_0$ to the height $h_1$, $h_2$, . . . (length in Y direction) of each structural element 40 being the same at 4:3, and (2) a flow channel structure in which flow channel width $y_0$=400 μm, number of structural elements 40=100, height $h_1$, $h_2$, . . . (length in Y direction) of each structural element 40=350 μm, width $x_1$, $x_2$ (length in X direction)=100 μm and interval $d_1$, $d_2$, . . . between adjacent structural elements 40=100 μm, with the flow channel width being wider than the flow channel structure of the above-mentioned basic structure and the ratio of flow path width $y_0$ to the height $h_1$, $h_2$, . . . (length in Y direction) of each structural element 40 being made to be 8:7.

Figure 16:
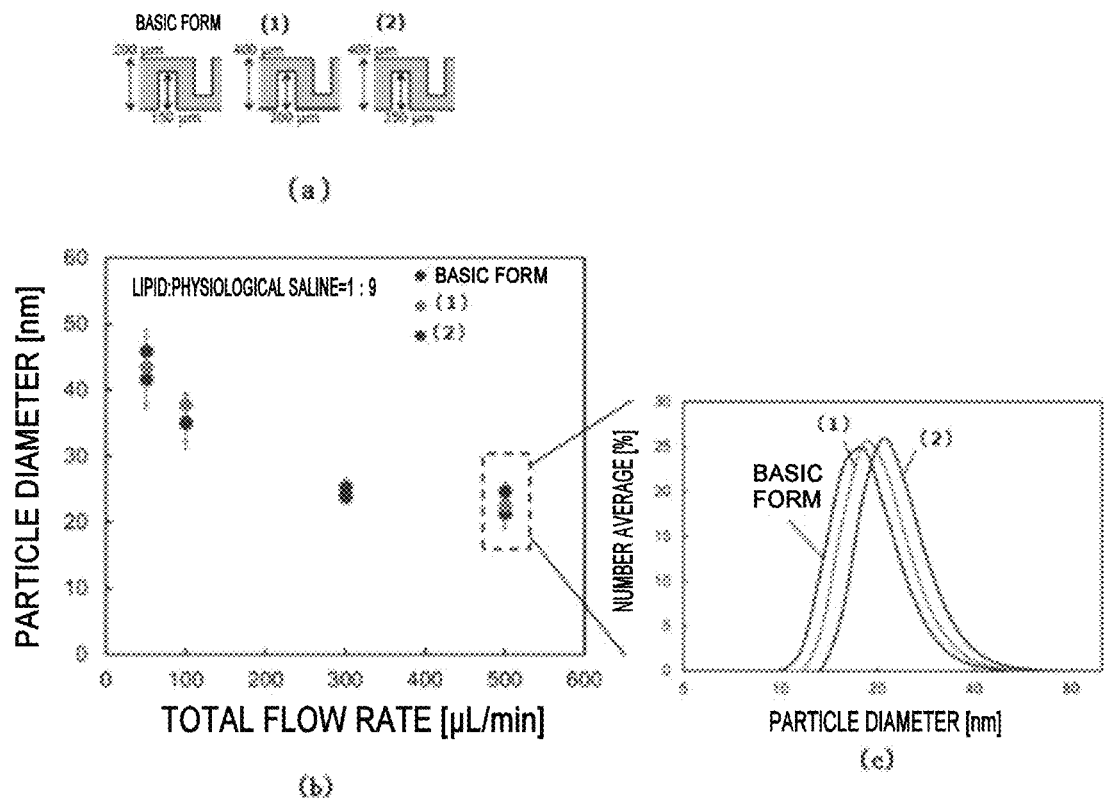
FIG. 16(a) is a drawing schematically showing the structure of a flow channel structure used in an example.
FIG. 16(b) is a graph indicating the relationship between the resulting structure and the particle diameter of formed lipid particles.
FIG. 16(c) is a graph indicating the relationship between the resulting structure and the particle size distribution of formed lipid particles.

A lipid solution (10 mg/ml of phosphatidylcholine solution in ethanol) was introduced from the first inlet channel 10 of these flow channel structures and physiological saline was introduced from the second inlet channel at a flow rate ratio of 1:9 while adjusting to a prescribed total flow rate, followed by forming lipid particles and investigating the particle diameter of the resulting lipid particles. Furthermore, a similar test was carried out in a flow channel structure of the same flow channel width but not having structural elements 40 and the results are shown in FIG. 16. As shown in FIGS. 6(b) and 6(c), there was no large effect on controllability of particle diameter even if the flow channel width $y_0$ was increased to 400 μm. In addition, the flow channel structure in which the ratio of the flow channel width $y_0$ to the height $h_1$, $h_2$, . . . (length in Y direction) of each structural element 40 was 4:3 allowed the obtaining of more favorable results than in the case of a ratio of 8:7 with respect to somewhat better controllability of particle diameter.

Example 10

The effect of the inclination of each structural element in the flow channel structure according to the present invention was investigated.

Figure 17:
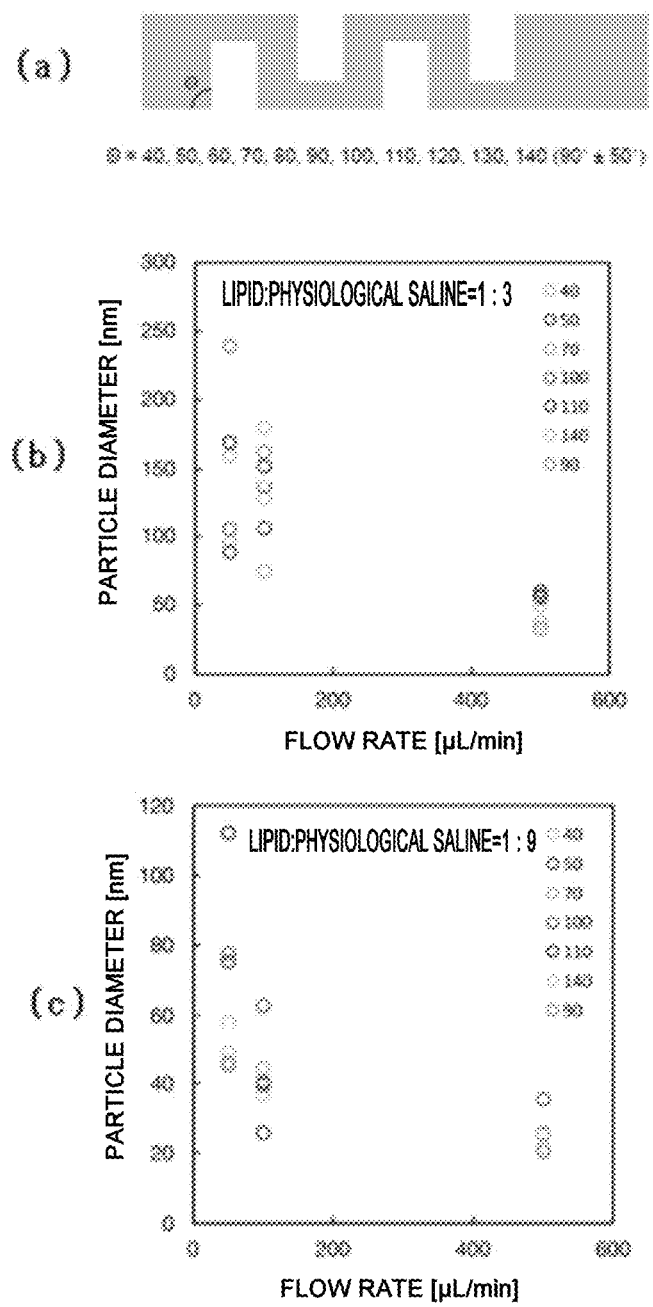
FIG. 17(a) is a drawing schematically showing the structure of a flow channel structure used in an example.
FIGS. 17(b) and 17(c) are graphs indicating the relationship between the resulting structure and the particle diameter of formed lipid particles.

Flow channel structures were fabricated that were composed such that the angle θ formed between the wall surface of each structural element and the direction of the flow channel (X direction) was 40°, 50°, 60°, 70°, 80°, 90°, 100°, 110°, 120°, 130° or 140° (90°±50° in flow channel structures having the basic configuration of flow channel width $y_0$=200 μm, number of structural elements 40=100, height $h_1$, $h_2$, . . . (length in Y direction) of each structural element 40=150 μm, width $x_1$, $x_2$ (length in X direction)=100 μm and interval $d_1$, $d_2$, . . . between adjacent structural elements 40=100 μm as shown in FIG. 17(a).

A lipid solution (10 mg/ml of phosphatidylcholine solution in ethanol) was introduced from the first inlet channel 10 of these flow channel structures and physiological saline was introduced from the second inlet channel at a flow rate ratio of 1:3 or 1:9 while adjusting to a prescribed total flow rate of 50 μl/min, 100 μl/min or 500 μl/min, followed by forming lipid particles and investigating the particle diameter of the resulting lipid particles. The results are shown in FIGS. 17(b) and 17(c). As shown in FIGS. 17(b) and 17(c), lipid particles having a prescribed particle diameter were able to be similarly formed even if the wall surface of each structural element was inclined within the range of about 90°±50° in the direction of the flow channel (X direction), and the particle diameter of the lipid particles was able to be confirmed to be controllable according to flow rate conditions.

Example 11

The effect of the number of fluid inlet channels in the flow channel structure according to the present invention was investigated. Flow channel structures were separately prepared having the same structure as the flow channel structure having the basic structure according to the present invention (each having one first inlet channel 10 and one second inlet channel 20; flow channel width $y_0$=200 μm, number of structural elements 40=100, height $h_1$, $h_2$, . . . (length in Y direction) of each structural element 40=150 μm, width $x_1$, $x_2$ (length in X direction)=100 μm and interval $d_1$, $d_2$, . . . between adjacent structural elements 40=100 μm) with the exception of having a shape in which two second fluid inlet channels 20a and 20b join together from both sides with the central first inlet channel 10 as schematically shown in FIG. 18(a).

In this flow channel structure having the two second fluid inlet channels 20a and 20b, a lipid solution (10 mg/ml phosphatidylcholine solution in ethanol) was introduced from the first inlet channel 10 and physiological saline was introduced from the second inlet channels 20a and 20b while adjusting so that the overall flow rate ratio of lipid solution to physiological saline was 1:3 and so that the flow rate ratio of the physiological saline respectively introduced from the second inlet channel 20a and the second inlet channel 20b was 1:1, 3:1, 1:3, 9:1 or 1:9, followed by investigating the particle diameter of the lipid particles.

In addition, for reference purposes, a lipid solution was introduced from the first inlet channel 10 and physiological saline was introduced from the second inlet channel 20 in the same manner as described above in a flow channel structure having the basic structure according to the present invention of one each of the first inlet channel 10 and the second inlet channel 20 while adjusting the overall flow rate ratio of lipid solution to physiological saline to 1:3, 1:5, 1:7, 1:9 or 1:20, followed by investigating the particle diameter of the lipid particles. The results are shown in FIGS. 18(b) and 18(c).

FIG. 18(b) is a graph indicating the effect on particle diameter of the lipid particles of changes in the flow rate ratio of physiological saline respectively introduced from the second inlet channel 20a and the second inlet channel 20b in the flow channel structure having two second fluid inlet channels 20a and 20b. Based on the results shown in FIG. 18(b), results were obtained in which changes in the flow rate ratio of physiological saline respectively introduced from the second inlet channel 20a and the second inlet channel 20b in the flow channel structure having two second fluid inlet channels 20a and 20b did not have that large of an effect on particle diameter of the resulting lipid particles.

FIG. 18(c) is a graph indicating the effect on particle diameter of the lipid particles in the case of using a flow channel structure having two second fluid inlet channels 20a and 20b and a flow channel structure having a single second inlet channel 20. Based on the results shown in FIG. 18(c), it was indicated that, as a result of having used a plurality (two) of second fluid inlet channels 2, the standard deviation of particle diameter of the lipid particles formed at a low flow rate decreased and there was little variation in particle diameter in comparison with the flow channel structure only having one first inlet channel and second inlet channel each. Furthermore, it was also indicated that, if the weight ratio of lipid solution to physiological saline is 1:3, the particle diameter of the resulting lipid particles tended to be smaller.

Example 12

The effect of the number of fluid inlet channels was investigated in aspects of the flow channel structure according to the present invention having different shapes (shape and arrangement of each structural element) of the bent flow channel site of the flow channel structure.

Namely, flow channel structures similar to that used in Example 11 were prepared for use as flow channel structures consisting of: (1) flow channel structure having a shape in which a single first inlet channel 10 and two second fluid inlet channels 20a and 20b join together therewith from both sides and in which the bent flow channel site is that of the above-mentioned basic structure (flow channel width $y_0$=200 μm, number of structural elements 40=100, height $h_1, h_2, \ldots$ (length in Y direction) of each structural element 40=150 μm, width $x_1, x_2$ (length in X direction)=100 μm and interval $d_1, d_2, \ldots$ between adjacent structural elements 40=100 μm), (2) flow channel structure having a shape in which a single first inlet channel 10 and two second fluid inlet channels 20a and 20b join together therewith from both sides and in which the bent flow channel site is such that flow channel width $y_0$=200 μm, number of structural elements 40=100, height $h_1, h_2, \ldots$ (length in Y direction) of each structural element 40=100 μm, width $x_1, x_2$ (length in X direction)=100 μm and interval $d_1, d_2, \ldots$ between adjacent structural elements 40=100 μm, (3) flow channel structure having a shape in which a single first inlet channel 10 and two second fluid inlet channels 20a and 20b join together therewith from both sides and in which the bent flow channel site is such that flow channel width $y_0$=200 μm, number of structural elements 40=100, height $h_1, h_2, \ldots$ (length in Y direction) of each structural element 40=150 μm, width $x_1, x_2$ (length in X direction)=100 μm and interval $d_1, d_2, \ldots$ between adjacent structural elements 40=500 μm, (4) flow channel structure having the basic structure according to the present invention (having one each of first inlet channel 10 and second inlet channel 20, and flow channel width $y_0$=200 μm, number of structural elements 40=100, height $h_1, h_2, \ldots$ (length in Y direction) of each structural element 40=150 μm, width $x_1, x_2$ (length in X direction)=100 μm and interval $d_1, d_2, \ldots$ between adjacent structural elements 40=100 μm), and (5) flow channel structure not having the structural elements 40 in a flow channel structure having the same flow channel width as the flow channel structure of (4) above provided for reference purposes.

In these five flow channel structures, a lipid solution (10 mg/ml phosphatidylcholine solution in ethanol) was introduced from the first inlet channel 10 and physiological saline was introduced from the second inlet channels 20a and 20b at a total flow rate of 50 μl/min while adjusting to an overall flow rate ratio of lipid solution to physiological saline of 1:3 and so that, in the flow channel structures of (1) to (3) above, the flow rate ratio of physiological saline respectively introduced from the second inlet channel 20a and the second inlet channel 20b is 1:1, 3:1, 1:3, 9:1 or 1:9 followed by forming lipid particles and investigating the particle diameter of the resulting lipid particles. The results obtained are shown FIGS. 19 and 20.

Figure 19:
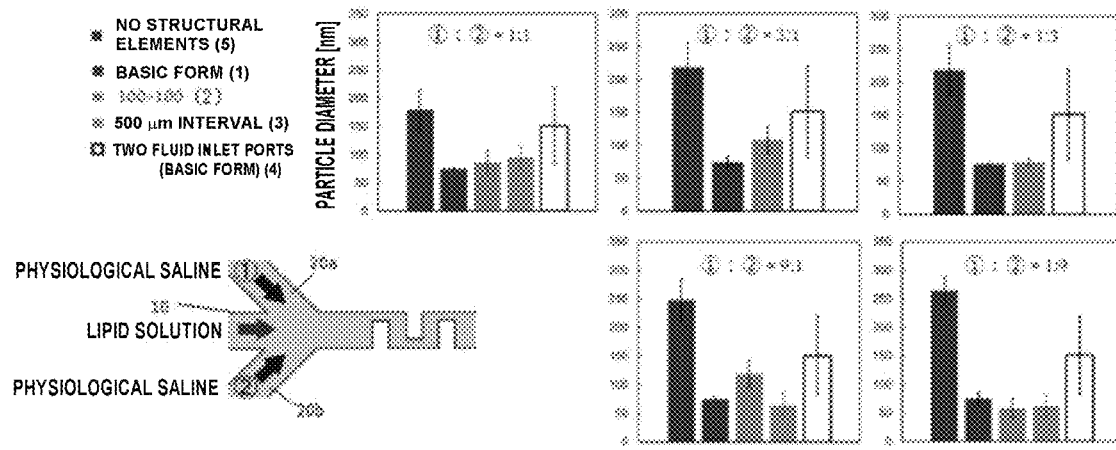
FIG. 19 is a graph indicating the relationship between the number of fluid inlet channels of a flow channel structure and the particle diameter of formed lipid particles obtained in an example.
Figure 20:
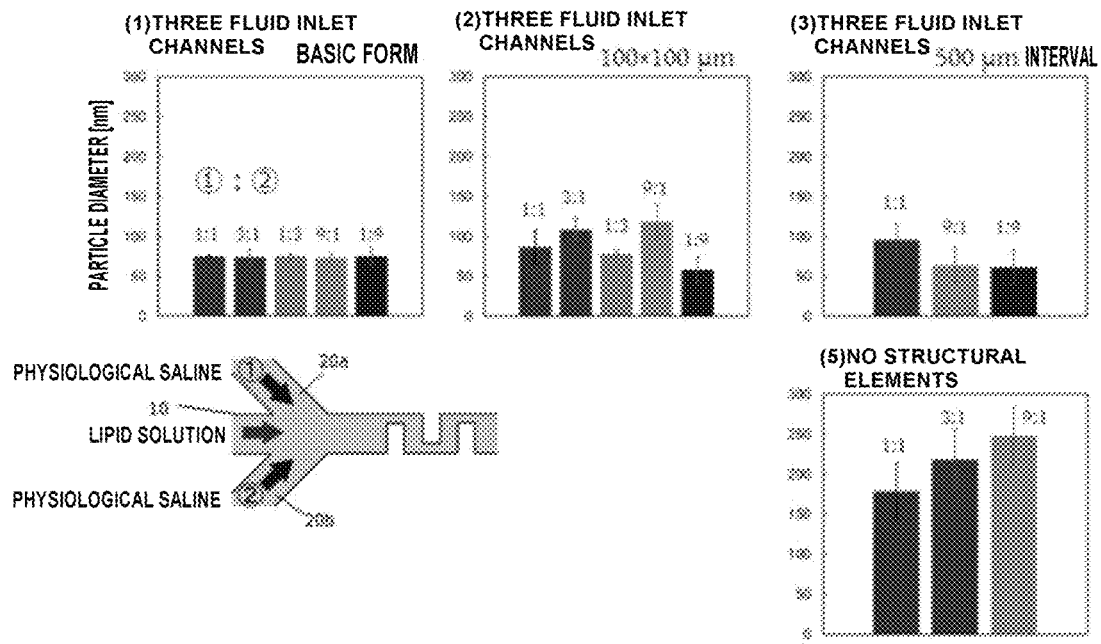
FIG. 20 is a graph indicating the relationship between the number of fluid inlet channels, shape of structural elements and arrangement of structural elements, and the particle diameter of formed lipid particles of a flow channel structure obtained in an example.

As shown in FIG. 19, in the case of using the flow channel structures of (1) to (3) above having a plurality (two) of second fluid inlet channels 2, the lipid diameter and standard deviation of the resulting lipid particles were both smaller in each case in comparison with the flow channel structure of (4) above which had only one first inlet channel and only one second inlet channel. In addition, as shown in FIGS. 19 and 20, particle diameter was indicated to undergo a relative change in the case of using the flow channel structures of (2) and (3) above according to the flow rate ratio of the physiological saline respectively introduced from the second inlet channel 20a and the second inlet channel 20b. On the other hand, particle diameter was indicated as not being greatly affected by flow rate ratio in the case of using the flow channel structure of (1) above.

Example 13

Figure 21:
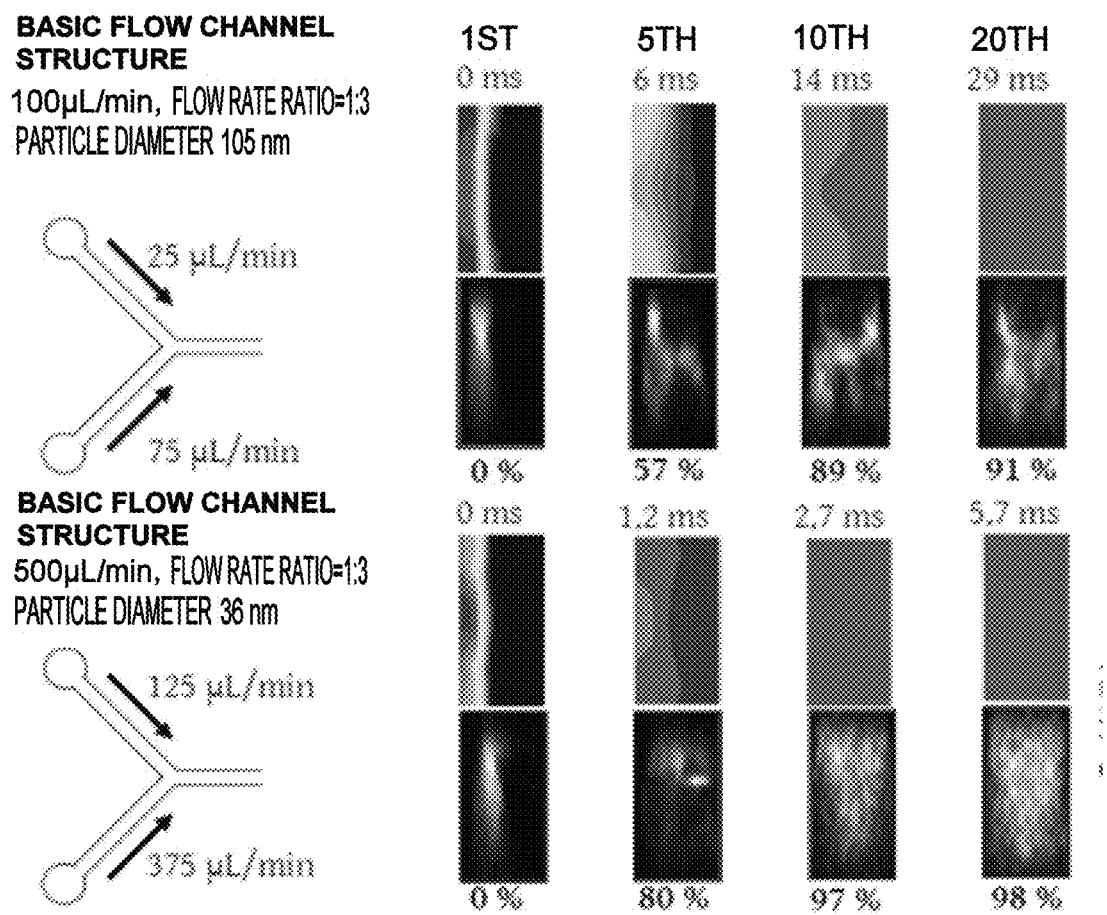
FIG. 21 indicates the results of a simulation showing the effects of structural elements attributable to differences in flow rates in a flow channel structure used in an example.

In order to simulate the diluted state of a lipid solution in a flow channel structure having the basic structure according to the present invention in the same manner as Example 6, ethanol, which is a water-miscible organic solvent of the lipid solution, and water as a dilution solvent, were allowed to flow into the flow channel structure at a flow rate ratio of 1:3 followed by simulating the flow thereof with the COMSOL Multiphysics general-purpose physics simulation software. Furthermore, in order to investigate the dilution process according to differences in total flow rate, the total flow rate was set to 100 μl/min and 500 μl/min. The results obtained are shown in FIG. 21. As shown in FIG. 21, a larger total flow rate was indicated to cause the lipid solution to be diluted more rapidly by the structural elements.

Example 14

Figure 22:
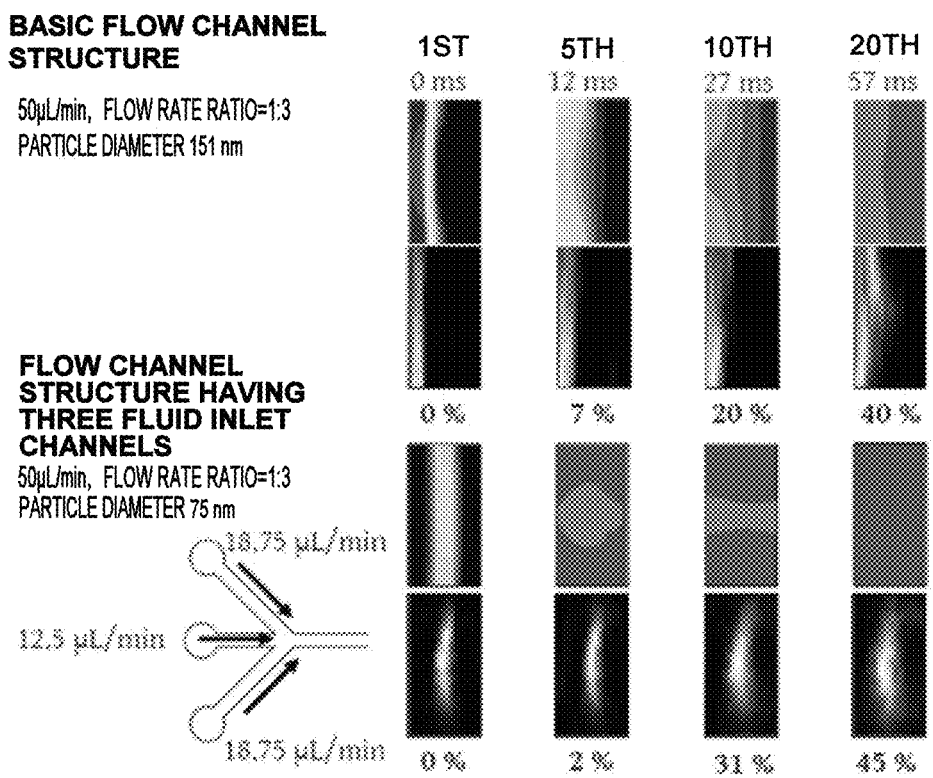
FIG. 22 indicates the results of a simulation showing the effects attributable to differences in the number of inlet channels in a flow channel structure used in an example.

In order to simulate (1) the diluted state of a lipid solution in the flow channel structure having the basic structure according to the present invention and (2) the diluted state of a lipid solution in a flow channel structure having the same structure as the above-mentioned flow channel structure having the basic structure with the exception of having a shape in which two second fluid inlets channels 20a and 20b join together with a central first inlet channel 10 in the same manner as that used in the above-mentioned Example 10, ethanol, which is a water-miscible organic solvent of the lipid solution, and water as a dilution solvent, were allowed to flow into the flow channel structure at a flow rate ratio of 1:3 and total flow rate of 50 μl/min followed by simulating the flow thereof with the COMSOL Multiphysics general-purpose physics simulation software in the same manner as the above-mentioned Example 6. Furthermore, the flow rate ratio of ethanol introduced by the second fluid inlet channel 20a and the second fluid inlet channel 20b in the flow channel structure of (2) above having two second fluid inlet channels 20a and 20b was 1:1. The results obtained are shown in FIG. 22. As shown in FIG. 22, the flow channel structure having a plurality (two) of second fluid inlet channels 2 was indicated to result in more rapid dilution in comparison with the flow channel structure having only one each of first and second fluid inlet channels.

Example 15

The effect of flow channel depth (three-dimensional spread) of the flow channel structure was investigated in the flow channel structure according to the present invention.

Figure 23:
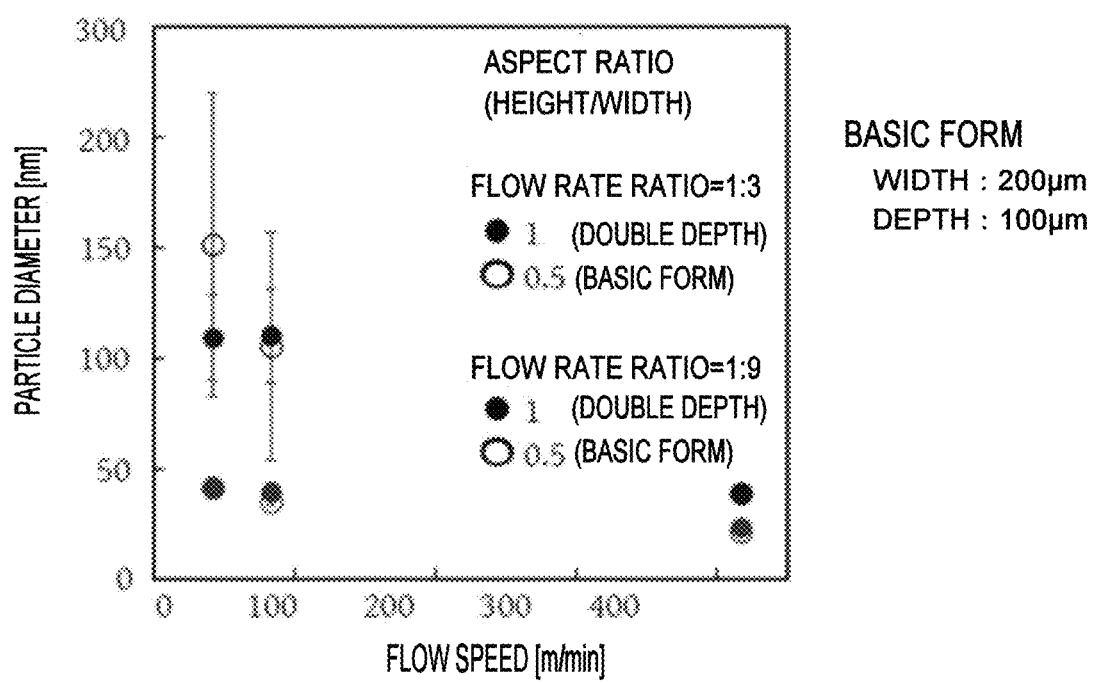
FIG. 23 is a graph indicating the relationship between the depth of a flow channel structure and the particle diameter of formed lipid particles obtained in an example.

Flow channel structures each having the basic structure according to the present invention (flow channel width $y_0$=200 μm, number of structural elements 40=100, height $h_1, h_2, \ldots$ (length in Y direction) of each structural element 40=150 μm, width $x_1, x_2,$ (length in X direction) of each structural element 40=100 μm and interval $d_1, d_2, \ldots$ between adjacent structural elements 40=100 μm), with one of the flow channel structures having a flow channel depth (direction of paper thickness in FIGS. 2 and 3) of 100 μm (flow channel depth/flow channel width=0.5) and the other having a flow channel depth of 200 μm (flow channel depth/flow channel width=1). A lipid solution (10 mg/ml phosphatidylcholine solution in ethanol) was introduced from the first inlet channel 10 of these flow channel structures and physiological saline was introduced from the second inlet channel at a flow rate ratio of 1:3 or 1:9 while adjusting so a prescribed total flow rate followed by forming lipid particles and investigating the particle diameter of the resulting lipid particles. The results obtained are shown in FIG. 23. As shown in FIG. 23, there was no change observed in particle diameter controllability even if the flow channel depth was doubled.

Example 16

An investigation was carried out as to whether the formation of polymer micelles using the flow channel structure according to the present invention can be the same as the formation of lipid particles.

Figure 24:
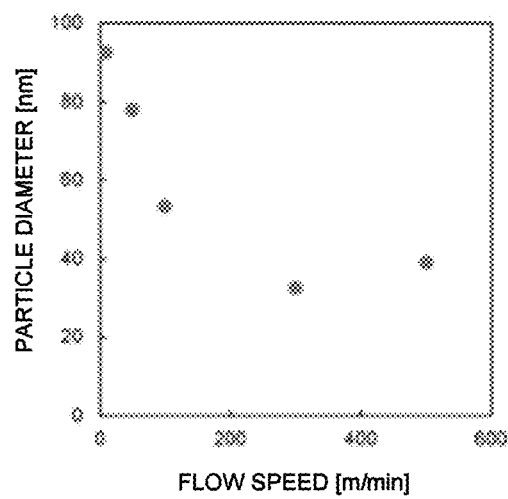
FIG. 24 is a graph indicating the relationship between differences in flow rate and the particle diameter of formed lipid particles obtained in an example.

A tetrahydrofuran solution of an amphipathic block copolymer in the form of polystyrene (PS)-polyethylene oxide (PO) block copolymer ($PS_{47}$-$PEO_{46}$-$PS_{47}$, number average molecular weight (Mn)=about 12000) (concentration of 1 mg of polymer in 1 ml of tetrahydrofuran) and ultrapure water as dilution medium were allowed to flow into the flow channel structure having the basic structure according to the present invention (flow channel width $y_0$=200 μm, number of structural elements 40=100, height $h_1, h_2, \ldots$ (length in Y direction) of each structural element 40=150 μm, width $x_1$, $x_2$ (length in X direction)=100 μm and interval $d_1, d_2, \ldots$ between adjacent structural elements 40=100 μm) at a flow rate ratio (polymer solution:water) of 1:10 and total flow speed of 10 μl/min, 50 μl/min, 100 μl/min, 300 μl/min or 500 μl/min followed by attempting to produce polymer micelles. As a result, as shown in FIG. 24, polymer micelles having a highly uniform size were able to be confirmed to be able to be formed at a particle diameter of 100 nm or less and particle diameter of the micelles was able to be confirmed to be able to be controlled according to flow rate conditions.

Example 17

Desired nano-sized lipid particles enclosing a nucleic acid-polycation complex were attempted to be formed in the flow channel structure having the basic structure as shown in FIG. 25(a).

As shown in FIG. 25(a), the flow channel structure used had a structure in which a flow channel structural unit having a bend flow channel site for a pretreatment process for forming core particles consisting of a nucleic acid-polycation complex (to be referred to as the "pretreatment flow channel structural unit") was connected on the upstream side and a flow channel structural unit having a bend flow channel site for carrying out the main process consisting of forming lipid particles (to be referred to as the "main process flow channel structural unit") was connected on the downstream side, and had a form in which the downstream outlet port of the pretreatment flow channel structural unit was connected to the second inlet channel (dilution medium inlet channel) of the main process flow channel structural unit.

Furthermore, the flow channel structure was fabricated such that conditions of the main process flow channel structural unit were such that flow channel width $y_0$=200 μm, height $h_1, h_2, \ldots$ (length in Y direction) of each structural element 40=150 μm, width $x_1, x_2,$ (length in X direction) of each structural element 40=100 μm and interval $d_1, d_2, \ldots$ between adjacent structural elements 40=100 μm were made to be constant while the number of structural elements 40 was made to be 20, and on the other hand, the flow channel conditions of the pretreatment process flow channel structural unit were also to be constant such that flow channel width $y_0$=200 μm, height $h_1, h_2, \ldots$ (length in Y direction) of each structural element 40=150 μm, width $x_1$, $x_2, \ldots$ (length in X direction) of each structural element 40=100 μm and interval $d_1, d_2, \ldots$ between adjacent structural elements 40=100 μm while the number of structural elements 40 was made to be 20.

First, a poly-L-lysine/buffer solution (0.1 mg/ml polylysine in 10 mM HEPES buffer, pH 7.4) was introduced from the first inlet channel of the pretreatment process flow channel structural unit and a nucleic acid/buffer solution (0.1 mg/ml DNA in 10 mM HEPES buffer, pH 7.4) was introduced from the second inlet channel at a flow rate ratio of 5:1 while adjusting to the prescribed total flow rate of the final main process followed by attempting to form core particles consisting of a nucleic acid-polycation complex. Moreover, a lipid solution (2 mg/ml DOPE/DSPE-PEG/DCP (5.2:2.4:0.4)) was introduced from the first inlet channel of the main process flow channel structural unit and treated solution discharged from the pretreatment process flow channel structural unit connected thereto was introduced directly from the second inlet channel of the main process flow channel structural unit at a flow rate ratio of 1:5 while adjusting to the prescribed total flow rate of the main process followed by forming lipid particles and investigating the particle diameter of the resulting lipid particles. The results are shown in FIG. 25(b). In this example, although core particles (particle diameter: 10 nm to 20 nm), which are the nucleic acid-polycation complex, were formed in the pretreatment process flow channel structural unit, and ultimately, as shown in FIG. 25(b), nano-sized lipid particles enclosing the core particles were able to be formed under any of the conditions, a larger total flow rate was indicated as resulting in a decrease in particle diameter.

Furthermore, the above-mentioned abbreviations have the meanings as indicated below.

HEPES=4-(2-hydroxyethyl)-1-piperazineethane sulfonic acid

DOPE=Dioleoylphosphatidylethanolamine

DSPE-PEG=Distearyl-phosphatidylethanolamine-polyethylene glycol

DCP=Dicetylphosphate

The invention claimed is:

1. A flow channel structure for forming nano-sized lipid particles or micelles,
    wherein in the flow channel structure, a mutually independent first inlet channel that introduces a first fluid and a second inlet channel that introduces a second fluid join together and have respectively fixed lengths on the upstream side thereof and a single dilution flow channel is formed towards the downstream side thereof,
    the dilution flow channel has a bent flow channel site that is bent two-dimensionally in at least a portion thereof, and
    the bent flow channel site is such that,
    in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$,
    at least two or more structural elements, which define flow channel width of the dilution flow channel by alternately protruding from both side surfaces of the dilution flow channel in opposition to the Y direction towards the center of the flow channel at a specific height $h_1, h_2, \ldots$ of $1/2y_0$ or more and less than $1y_0$ in an approximate Y direction (approximate +Y direction or approximate −Y direction) and at a specific width $x_1, x_2, \ldots$ in the X direction, are provided at specific intervals $d_1, d_2, \ldots$, wherein the flow channel width $y_0$ is 100 μm to 200 μm, the height of each structural element $h_1, h_2, \ldots$ is $1/2y_0$ or more than $3/4y_0$ or less, the width of each structural element $x_1, x_2, \ldots$ is 70 μm to 100 μm, and the interval between each structural element $d_1, d_2, \ldots$ is 100 μm to 500 μm.

2. The flow channel structure according to claim 1, wherein the structural elements are provided from 10 to 100.

3. The flow channel structure according to claim 1, wherein the distance from the confluence of the first inlet channel and the second inlet channel to the upstream end of the first structural element is defined corresponding to the set speed of the dilution fluid so that dilution fluid at a set speed flowing therebetween passes through in 0.1 seconds or less.

4. The flow channel structure according to claim 1, wherein a plurality of flow channels is respectively provided as the first inlet channel and/or the second inlet channel.

5. The flow channel structure according to claim 1, wherein the approximate Y direction is a direction that intersects the flow channel direction (X direction) at an angle of 40° to 140°.

6. The flow channel structure according to claim 1, wherein at least one of the first inlet channel that introduces a first fluid and the second inlet that introduces a second fluid is connected to a flow channel for a pretreatment process located at the upstream side thereof and the flow channel for a pretreatment process has a similar structure to the flow channel structure according to claim 1.

7. A lipid particle or micelle formation method for forming nano-sized lipid particles or micelles by diluting a lipid solution or amphipathic substance solution with a dilution medium in a flow channel structure,
    wherein a flow channel structure according to claim 1 is used as the flow channel structure and the lipid solution or amphipathic substance solution are introduced from one of the first inlet channel and second inlet channel of the flow channel structure and the dilution solvent is introduced from the other inlet channel at a total flow rate of 1 μl/min to 100 ml/min.

8. The flow channel structure according to claim 6, wherein an outlet of the dilution flow channel of the flow channel for a pretreatment process is connected to the first inlet channel or the second inlet channel.

9. The flow channel structure according to claim 1, wherein a structural element locating at the most upstream side of the dilution flow channel is disposed on the side wall at the side of the second inlet channel, and
    the flow channel structure is for use in a method in which a lipid solution or amphipathic substance solution flows from the first inlet channel and a dilution medium flows from the second inlet channel to dilute a lipid solution or amphipathic substance solution in a flow channel structure to form nano-sized lipid particles or micelles.

10. The flow channel structure according to claim 9, wherein the ratio of the flow rate of the lipid solution or amphipathic substance solution to the flow rate of the dilution medium is 1:3 to 1:10.

11. The method according to claim 7, wherein in the flow channel structure, a structural element locating at the most upstream side of the dilution flow channel is disposed on the side wall at the side of the second inlet channel, and a lipid solution or amphipathic substance solution flows from the first inlet channel and a dilution medium flows from the second inlet channel to dilute a lipid solution or amphipathic substance solution in the flow channel structure to form nano-sized lipid particles or micelles.

12. The method according to claim 7, wherein the ratio of the flow rate of the lipid solution or amphipathic substance solution to the flow rate of the dilution medium is 1:3 to 1:10.

13. The method according to claim 7, wherein particle size of the nano-sized lipid particles or micelles is in a range of 20 nm to 100 nm.

14. A flow channel structure for forming nano-sized lipid particles or micelles,
    wherein the flow channel structure, a mutually independent first inlet channel that introduces a first fluid and a second inlet channel that introduces a second fluid join together and have respectively fixed lengths on the upstream side thereof and a single dilution flow channel is formed towards the downstream side thereof,
    the dilution flow channel has a bent flow channel site that is bent two-dimensionally in at least a portion thereof, and
    the bent flow channel site is such that,
    in the case the axial direction of the dilution flow channel upstream therefrom or the direction in which it extends is defined as the X direction, the widthwise direction of the dilution flow channel that perpendicularly intersects with this X direction is defined as the Y direction, and the flow channel width of the dilution flow channel upstream therefrom is defined as $y_0$,
    at least two or more structural elements, which define flow channel width of the dilution flow channel by alternately protruding from both side surfaces of the dilution flow channel in opposition to the Y direction towards the center of the flow channel at a specific height $h_1, h_2, \ldots$ of $1/2y_0$ or more and less than $1y_0$ in an approximate Y direction (approximate +Y direction or approximate −Y direction) and at a specific width $x_1, x_2, \ldots$ in the X direction, are provided at specific intervals $d_1, d_2, \ldots$, wherein the flow channel width $y_0$ is 20 μm to 1000 μm, the width of each structural element $x_1, x_2, \ldots$ is 20 μm to 1000 μm, and the interval $d_1, d_2, \ldots$ between each structural element is 20 μm to 1000 μm wherein the lipid particles formed have a diameter of 10 to 100 nm.

15. The flow channel structure according to claim 14, wherein the height of each structural element $h_1, h_2, \ldots$ is $1/2y_0$ or more to $3/4y_0$ or less.

16. The flow channel structure according to claim 14, wherein the structural elements are provided from 10 to 100.

17. The flow channel structure according to claim 14, wherein the distance from the confluence of the first inlet channel and the second inlet channel to the upstream end of the first structural element is defined corresponding to the set speed of the dilution fluid so that dilution fluid at a set speed flowing therebetween passes through in 0.1 seconds or less.

18. The flow channel structure according to claim 14 wherein a plurality of flow channels is respectively provided as the first inlet channel and/or the second inlet channel.

19. The flow channel structure according to claim 14, wherein the approximate Y direction is a direction that intersects the flow channel direction (X direction) at an angle of 40° to 140°.

20. The flow channel structure according to claim 14, wherein at least one of the first inlet channel that introduces a first fluid and the second inlet that introduces a second fluid is connected to a flow channel for a pretreatment process located at the upstream side thereof and the flow channel for a pretreatment process has a similar structure to the flow channel structure according to claim 14.

21. The flow channel structure according to claim 20, wherein an outlet of the dilution flow channel of the flow channel for a pretreatment process is connected to the first inlet channel or the second inlet channel.

22. The flow channel structure according to claim 14, wherein a structural element locating at the most upstream side of the dilution flow channel is disposed on the side wall at the side of the second inlet channel, and the flow channel structure is for use in a method in which a lipid solution or amphipathic substance solution flows from the first inlet channel and a dilution medium flows from the second inlet channel to dilute a lipid solution or amphipathic substance solution in a flow channel structure to form nano-sized lipid particles or micelles.

23. The flow channel structure according to claim 22, wherein the ratio of the flow rate of the lipid solution or amphipathic substance solution to the flow rate of the dilution medium is 1:3 to 1:10.

* * * * *